(12) United States Patent
Sharifzadeh et al.

(10) Patent No.: US 9,968,250 B2
(45) Date of Patent: May 15, 2018

(54) AUTOFLUORESCENCE IMAGING OF MACULAR PIGMENT: IMAGE QUALITY CRITERIA AND CORRECTIONS

(71) Applicant: Image Technologies Corporation, Salt Lake City, UT (US)

(72) Inventors: Mohsen Sharifzadeh, Salt Lake City, UT (US); Werner Gellermann, Salt Lake City, UT (US)

(73) Assignee: Image Technologies Corporation, Salt Lake City, UT (US)

( * ) Notice: Subject to any disclaimer, the term of this patent is extended or adjusted under 35 U.S.C. 154(b) by 32 days.

(21) Appl. No.: 14/536,356

(22) Filed: Nov. 7, 2014

(65) Prior Publication Data

US 2015/0238075 A1 Aug. 27, 2015

Related U.S. Application Data

(60) Provisional application No. 61/943,942, filed on Feb. 24, 2014.

(51) Int. Cl.
| | |
|---|---|
| A61B 3/00 | (2006.01) |
| A61B 3/12 | (2006.01) |
| A61B 3/14 | (2006.01) |
| A61B 3/10 | (2006.01) |

(52) U.S. Cl.
CPC ............ *A61B 3/0025* (2013.01); *A61B 3/10* (2013.01); *A61B 3/12* (2013.01); *A61B 3/14* (2013.01)

(58) Field of Classification Search
USPC ................................................ 351/200–246
See application file for complete search history.

(56) References Cited

U.S. PATENT DOCUMENTS

| | | | |
|---|---|---|---|
| 7,914,147 B2 | 3/2011 | Sharifzadeh et al. | |
| 8,078,267 B2 | 12/2011 | Gellerman et al. | |
| 8,475,438 B2 * | 7/2013 | Larsen | A61F 9/008 606/11 |

(Continued)

OTHER PUBLICATIONS

International Search Report and Written Opinion issued for International Application No. PCT/US2015/016942 dated May 21, 2015.

(Continued)

*Primary Examiner* — Darryl J Collins
*Assistant Examiner* — Journey Sumlar
(74) *Attorney, Agent, or Firm* — Austin Rapp

(57) ABSTRACT

A method, system, and computer program product are disclosed for diagnosing a condition of an eye such as macular degeneration and/or cataracts. The system may include an optical system, which may project light at an eye and record lipofuscin fluorescence from a retina of the eye to form an image of the retina. A computing device may process the image to apply one or more image acceptance criteria and/or one or more image clarity criteria. If the image fails to meet the one or more image acceptance criteria, the image may be re-taken. Based on the level of conformance of the image to the one or more image clarity criteria, the system may indicate that the macular pigment level cannot be provided with confidence, indicate that the eye likely has one or more cataracts, and/or calculate and provide the macular pigment content based on a correction factor, if needed.

17 Claims, 19 Drawing Sheets

(56) References Cited

U.S. PATENT DOCUMENTS

| | | |
|---|---|---|
| 2003/0002014 A1 | 1/2003 | Grant |
| 2006/0244913 A1 | 11/2006 | Gellerman et al. |
| 2008/0266520 A1 | 10/2008 | Spaide |
| 2010/0049057 A1 | 2/2010 | Gellerman et al. |
| 2010/0284576 A1 | 11/2010 | Tosa |
| 2011/0007270 A1 | 1/2011 | Sarver et al. |
| 2012/0257164 A1 | 10/2012 | Zee et al. |
| 2014/0044319 A1 | 2/2014 | Derakhshani et al. |
| 2015/0238074 A1 | 8/2015 | Sharifzadeh et al. |

OTHER PUBLICATIONS

Sharifzadeh et al., "Nonmydriatic fluorescence-based quantitative imaging of human macular pigment distributions," J. Opt. Soc. Am., vol. 23, No. 10, pp. 2373-2387, Oct. 2006.

Stringham, "Macular pigment and visual performance in glare: benefits for photostress recovery, disability glare, and visual discomfort," Invest. Ophthalmol. Vis. Sci., vol. 52, No. 10, pp. 7406-7415, Sep. 2011.

Dlori, "Autofluorescence method to measure macular pigment optical densities fluorometry and autofluorescence imaging," Archives of Biochemistry and Biophysics, 430, pp. 156-162, 2004.

Sasamoto et al., "Effect of cataract in evaluation of macular pigment optical density by autofluorescence spectrometry," Invest. Ophthalmol. Vis. Sci., vol. 52, No. 2, pp. 927-932, Feb. 2011.

Chylack et al., "The Lens Opacities Classification System III," Arch Ophthalmol., vol. 111, pp. 831-836, Jun. 1993.

Chylack et al. "Lens Opacities Classification System," Arch Ophthalmol., vol. 106, pp. 330-334, Mar. 1988.

Office Action issued for U.S. Appl. No. 14/204,742 dated Jul. 31, 2015.

Delori et al., "Macular Pigment Density Measured by Autofluorescence Spectrometry: Comparison with Reflectometry and Heterochromatic Flicker Photometry", JOSA vol. 18, No. 6, pp. 1212-1230, Jun. 2001.

Sharifzadeh et al., "Autofluorescence Imaging of Macular Pigment: Influence and Correction of Ocular Media Opacities," Journal of Biomedical Optics, vol. 19(9), pp. 096010-1-096010-10, Sep. 2014.

\* cited by examiner

Autofluorescence Image Processing

Derived MPOD levels along nasal-temporal meridian

Derived spatial MPOD distribution with gray-scale intensities

Illumination Characteristics
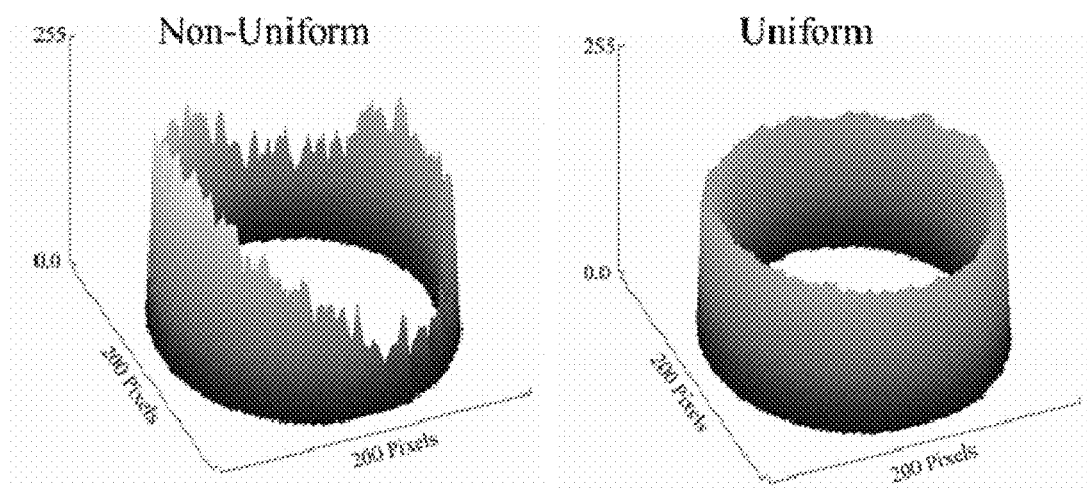
Fig. 7A     Fig. 7B
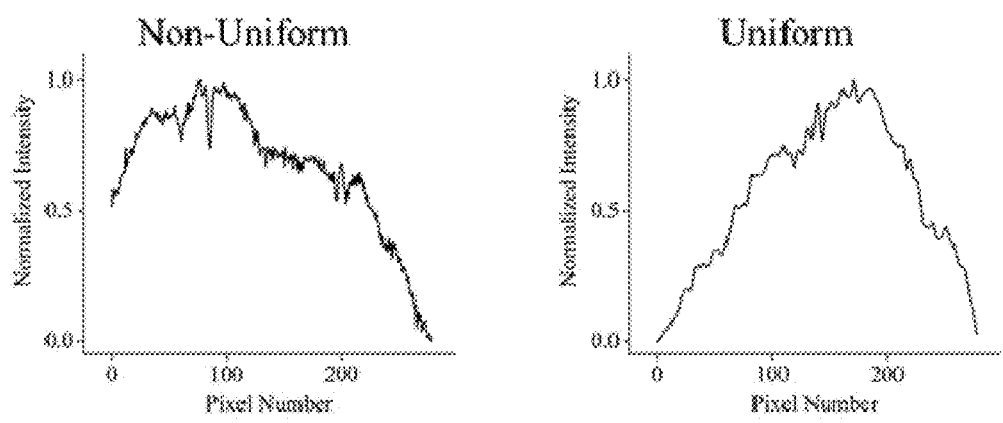
Fig. 7C     Fig. 7D

Before Cataract Surgery  After Cataract Surgery
Raw Images
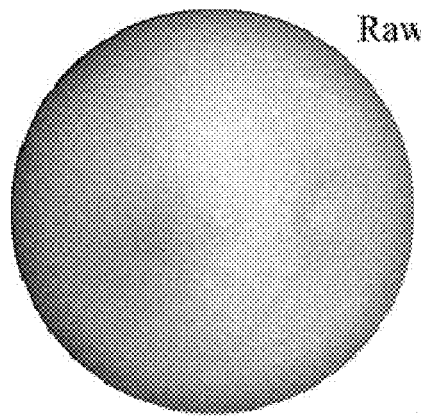 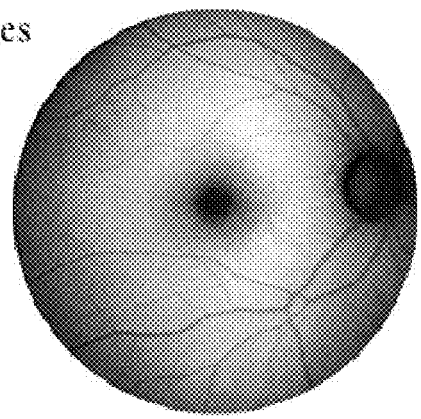
Fig. 8A  Histograms  Fig. 8B
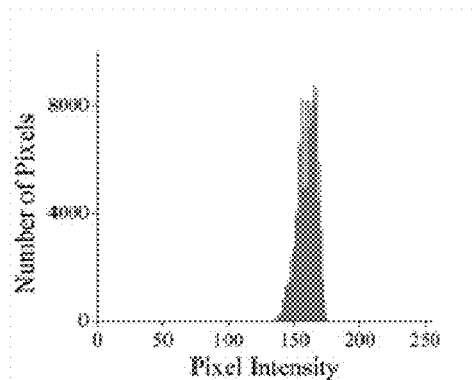 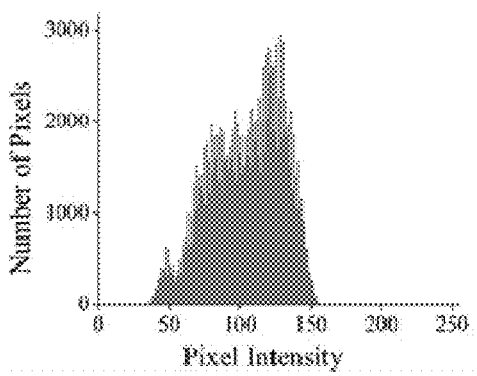
Fig. 8C  Central Line Plots  Fig. 8D
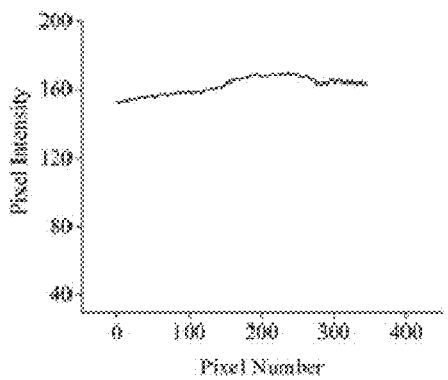 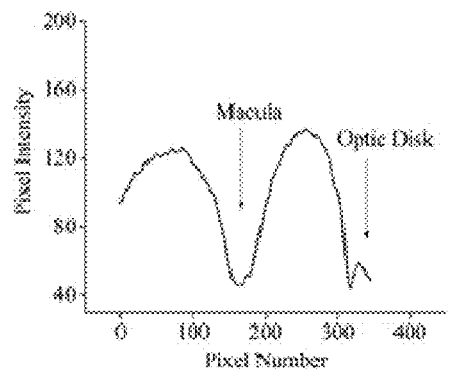
Fig. 8E  Fig. 8F

Before Cataract Surgery  After Cataract Surgery
Raw images
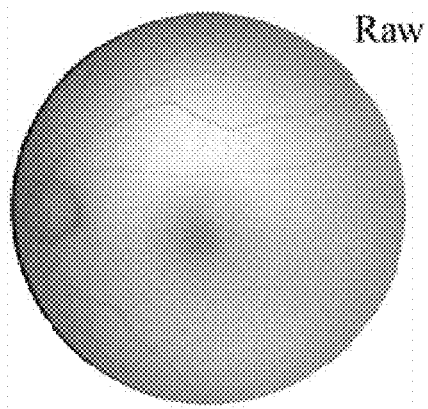 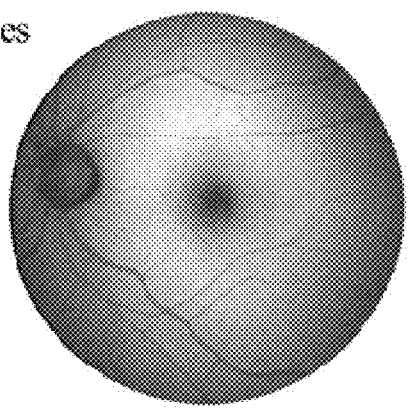
Fig. 9A   Histograms   Fig. 9B
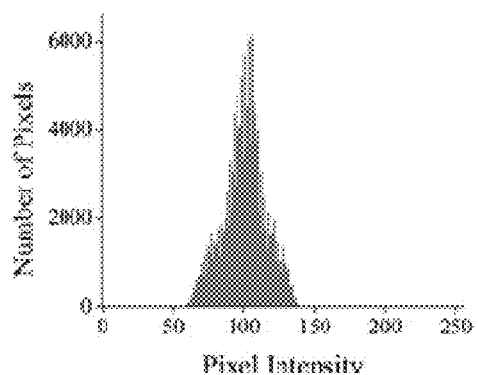 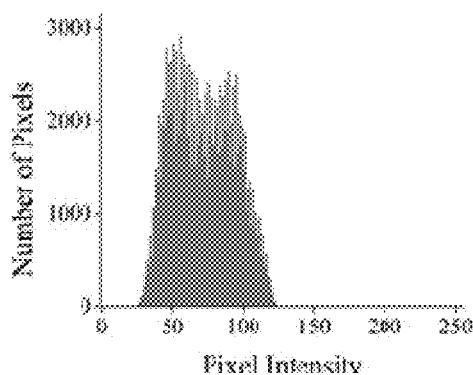
Fig. 9C   Central Line Plots   Fig. 9D
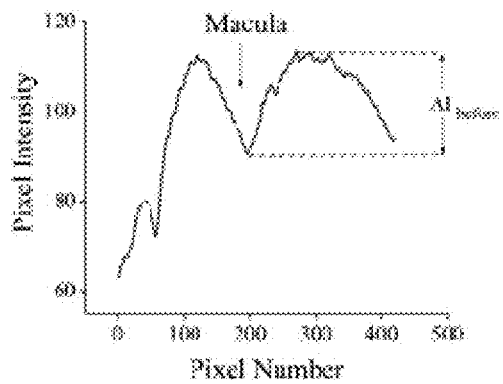 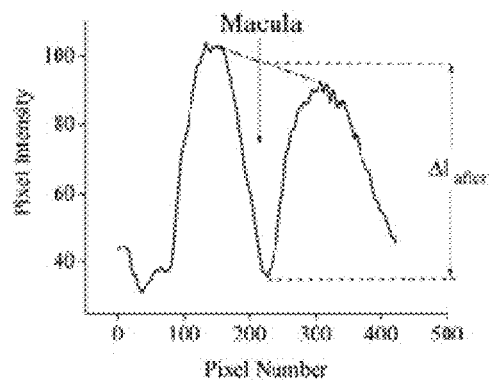
Fig. 9E   Fig. 9F

Subject 1

Subject 2

LOCS III scores: 3, 3 and 2
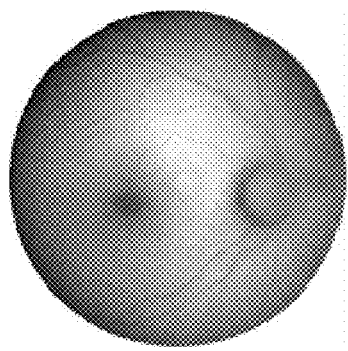 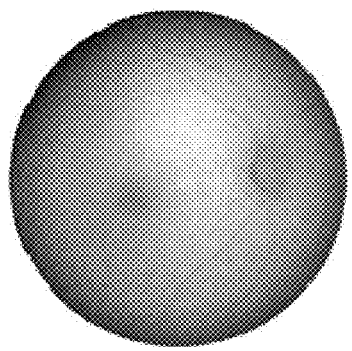 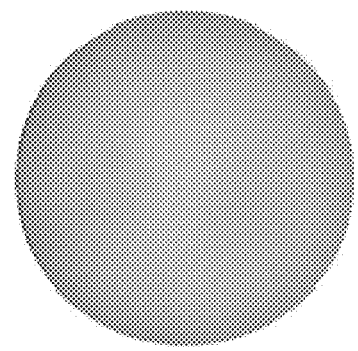
*Fig. 16A*        *Fig. 16B*        *Fig. 16C*
LOCS III scores: 3, 2 and 2
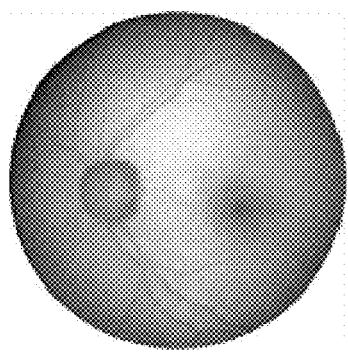 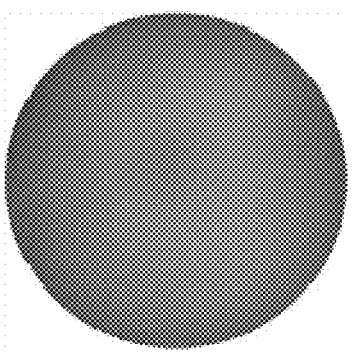 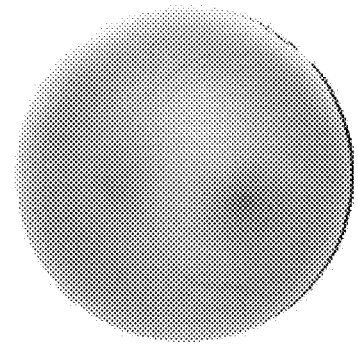
*Fig. 16D*        *Fig. 16E*        *Fig. 16F*
LOCS III scores: 3, 3 and 3
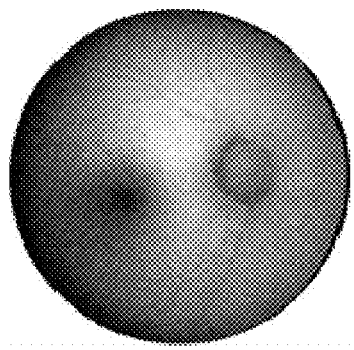 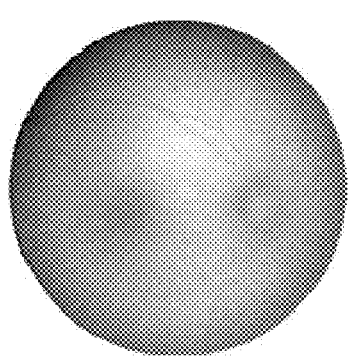 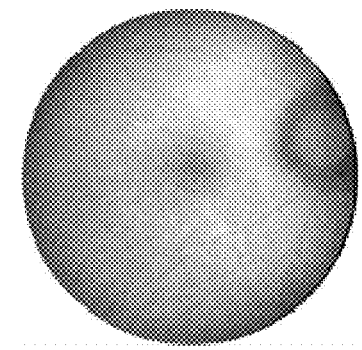
*Fig. 16G*        *Fig. 16H*        *Fig. 16I*

AUTOFLUORESCENCE IMAGING OF MACULAR PIGMENT: IMAGE QUALITY CRITERIA AND CORRECTIONS

RELATED APPLICATIONS

This application is related to and claims priority from U.S. Provisional Patent Application Ser. No. 61/943,942, filed Feb. 24, 2014, for "AUTOFLUORESCENCE IMAGING OF MACULAR PIGMENT: IMAGE QUALITY CRITERIA AND CORRECTIONS," which is incorporated herein by reference.

TECHNICAL FIELD

The present invention relates to optical techniques for measuring the levels of chemical compounds in biological tissue. More specifically, the invention relates to the noninvasive optical detection and measurement of levels of macular carotenoids derived from spectrally selective lipofuscin fluorescence ("autofluorescence") spectroscopy. The influences of tissue opacities potentially present in ocular media located anterior to the retina, most importantly from cataracts in the natural lens, are investigated in their effects on the quantitative information on macular pigment characteristics that are derivable from the autofluorescence images.

BACKGROUND

The healthy adult human retina contains high concentrations of blue-light absorbing carotenoid compounds in its macular region, which is the ~1 mm diameter central retina location around the fovea. The latter is concentrated with the cone photoreceptors, which are responsible for high-acuity color vision. Known as macular pigment, MP, the carotenoids consist of three sub-species: lutein, zeaxanthin, and meso-zeaxanthin, all located in the retinal layer system anterior to the photoreceptor outer cell segments and anterior to the retinal pigment epithelium. Due to its location in the outer part of the retinal layer system, the MP is thought to shield the deeper vulnerable tissue layers from light-induced damage. This is achieved by the MP by effectively absorbing the photo-ionizing, short, deep blue to UV wavelengths of ambient light, which would otherwise reach the deeper retinal layers. The MP carotenoids are also thought to protect the tissue cells in their immediate vicinity through their well-known function as antioxidants. Much research carried out over the last two decades has investigated the role of the macular carotenoids in the prevention of Age Related Macular Degeneration ("AMD"), and more recently their role is also investigated in the improvement of visual acuity via reduction of deleterious glare effects.

Several methodologies for non-invasive optical MP assessment are currently pursued to facilitate screening of large subject populations for MP status, to track changes over time, and/or to monitor MP uptake in response to supplementation. These include the relatively widely used psychophysical method of Heterochromatic Flicker Photometry, and three emerging imaging methods permitting a quantitative objective measurement of MP levels at any macular location and in this way to obtain the MP distribution over the whole macular region. The three imaging methods include direct MP detection via Resonance Raman Spectroscopy, indirect MP detection via lipofuscin fluorescence excitation spectroscopy, also known as "autofluorescence" spectroscopy, and indirect detection via fundus reflection spectroscopy. A particular autofluoresence imaging approach is already implemented in a commercially available laser ophthalmoscopy platform that uses a 488 nm argon laser in raster-scanning mode for lipofuscin fluorescence excitation in combination with confocal detection of the fluorescence ("Model HRA", Heidelberg Engineering, Inc., Germany); a reflection based imaging approach with conventional blue light source excitation is implemented in a commercially available fundus camera platform ("Visucam", Zeiss Inc., Germany).

In autofluorescence spectroscopy, lipofuscin chromophores in the retinal pigment epithelial layer are excited, respectively, with wavelengths that lie within a certain blue spectral region where the absorption band of lipofuscin overlaps with the absorption band of the MP carotenoids, and with slightly longer wavelengths that still lie within the absorption region of lipofuscin but outside the absorption range of MP. This can be realized, respectively, with narrow-band 488 nm blue and 532 nm green laser light sources, with suitably filtered conventional arc-lamp or tungsten-halogen light sources, with light emitting diodes (LEDs), or with suitable sets of wavelengths provided by other light sources. Green light excitation leads to un-attenuated lipofuscin fluorescence in the macular region as well as in all peripheral regions of the retinal hemisphere. Blue light excitation, in contrast, leads to un-attenuated lipofuscin fluorescence only in the peripheral regions; in the macular region, the fluorescence intensity is now attenuated due to blue-light absorbing MP carotenoids. By comparing the lipofuscin fluorescence intensities obtained with both excitation wavelengths in foveal and peripheral retina regions, the single pass absorption of the MP can be obtained, quantified as the optical density, OD. Specifically, the MPOD is calculated for any particular location inside the macular region as the negative decimal logarithm of the ratio of the lipofuscin intensity at that macular location, $I_{min}$, to the lipofuscin intensity at peripheral locations, $I_{max}$. The lipofuscin fluorescence, which has a high oscillator strength and which occurs in a far red to near infrared broad wavelength band, is relatively easily detected in retinal (fundus) imaging configurations with a charge-coupled detector array (CCD array) under conveniently short light exposure conditions. In the healthy retina, lipofuscin is usually distributed uniformly over the retinal pigment epithelial layer. It has been shown that under this condition, two-wavelength AFI imaging with blue and green excitation light leads to the same MP results as one-wavelength AFI imaging with blue light excitation, i.e. the step of testing the uniformity of the lipofuscin distribution with the green "reference" excitation can be omitted.

Issues in the derivation of MP characteristics via autofluorescence imaging, AFI, can arise if absorption, fluorescence, and scattering effects are present due to the presence of other compounds than the lipofuscin and carotenoid chromophores of interest. Potentially these other compounds can interfere with the optical detection scheme for MP.

One issue is the fluorescence of the natural lens, which occurs at wavelengths in the visible to far red wavelength region under the autofluorescence excitation conditions described above. It has been shown that this fluorescence can be largely avoided by limiting the lipofuscin fluorescence detection to the long-wavelength shoulder of its emission band, i.e. to wavelengths above approximately 700 nm. Under these detection conditions the image contrast between lipofuscin intensities in the macular region and the periphery is significantly improved.

Another issue is the question of potential opacities in anterior ocular media, most importantly in the natural lens, where cataracts, often found in elderly subjects, could lead to AFI contrast degradation due to excessive scattering. It is necessary therefore to investigate the quantitative influence of media opacities, at least due to the predominant lens cataracts, on the achievable MP levels in AFI imaging, and possibly to derive correction factors for the AFI images in the presence of pathologies.

SUMMARY

The present invention may provide qualitative and/or quantitative AFI image acceptance criteria to determine whether an AFI image is acceptable or needs to be re-taken. The present invention may also provide qualitative and/or quantitative AFI image clarity criteria that can be used to determine whether any ocular media opacity present in the eye would prevent the provision of an accurate MPOD level. Additionally or alternatively, the present invention may provide derivation of correction factors to the AFI-derived nominal MPOD levels in the presence of ocular media opacities.

In order to formulate the acceptance criteria and/or correction factors mentioned above, a clinical trial was conducted that involved AFI-based measurements of MPOD levels in a large subject population (93 patients) before and after cataract surgery. As a measurement platform, a modified non-mydriatic fundus camera was used. Two-dimensional lipofuscin intensity pixel maps (AFI images) were recorded with a high sensitivity CCD camera at wavelengths above 700 nm and 43° field of view—detection conditions under which the subject-specific MP characteristics are ideally visible as a localized, high contrast, central image region of attenuated fluorescence. Software routines were used that compare pixel fluorescence intensities from the peripheral retina at approximately 10° eccentricity with pixel intensities in the macular region, and in this way derive MPOD levels as quantitative measures for individual MP characteristics. The MP characteristics can be conveniently displayed as the maximum MPOD level of the MP distribution in the macula, as a line plot of MP levels across suitable meridians, such as along nasal-temporal and inferior-superior meridians, as a pseudo-colored 3-dimensional spatial MP distribution, as the MPOD volume under the distribution, and/or as a combination of these results.

One embodiment of the invention may use localized image contrast generated by retinal blood vessels located in the spatial vicinity of the macular region as an AFI image quality criterion. In healthy eyes with unobstructed light paths, i.e. in the absence of media opacities, the retinal blood vessels may be clearly distinguishable in the AFI images as sharp filament-like regions of heavily attenuated lipofuscin intensities, which may be due to the absorption of the excitation wavelengths used in AFI imaging by the vessel blood. Typically, the contrast between pixel intensities inside and outside those blood vessel regions in the healthy retina may have a certain acceptable ratio. In the presence of media opacities, such as absorption and scattering caused by cataracts, non-uniformities of the vitreous humor, etc., the measureable blood vessel contrast can be severely degraded. Comparisons of the measurable blood vessel contrasts before and after cataract surgery may allow one to establish quantitative comparisons for the effects of the opacities.

Another embodiment of the current invention may use more general image contrast recorded in the AFI pixel intensity maps. The complete AFI image or certain pixel areas of the AFI images can be strategically chosen for assessment of intensity variations. These may be quantified via calculations of histograms of the numbers of pixels with identical intensity values, or via line plots of pixel intensities along strategically chosen directions through the image/intensity pixel map.

As examples, an image histogram can be calculated for the complete AFI map, or the deviations of pixel intensities from average values can be quantified for directions such as the nasal-temporal meridian running across the AFI map through the center of the macula. In general, for clear anterior optical media, large variations in pixel contrast may be seen in the images when progressing from regions of high lipofuscin pixel intensities in the peripheral image areas to attenuated pixel intensities in the macular region, or across retinal blood vessels. In cases with media opacities, the combined absorption and scattering effects may degrade the achievable pixel contrasts in the images to the effect where their intensities across the meridian are becoming nearly constant. The loss of image contrast can therefore be used as a criterion for the presence of scattering media opacities such as cataracts.

In one exemplary method, the AFI image may be taken by projecting light into the eye and recording fluorescence of light from the retina. The AFI image may be processed to determine whether it meets one or more image acceptance criteria, which may include proper focus, proper illumination, centering of the macula, and/or other criteria. If the AFI image fails to meet any of the AFI image criteria, the AFI image may be retaken.

Once an AFI image is deemed acceptable, it may be processed to determine whether it meets one or more image clarity criteria, which may include blood vessel contrast and histogram analysis. If the AFI image fails to meet any of the image clarity criteria, an indication may be provided that the MPOD level for the eye cannot be reliably provided and/or that the eye likely has one or more ocular media opacities such as cataracts.

If the AFI image does meet the image clarity criteria, a correction factor may be used, as needed, to correct the measured MPOD level to account for the presence of any such ocular media opacities that are not severe enough to prevent effective measurement of the MPOD level of the eye. Thus, relatively accurate MPOD levels in eyes with mild to moderate cataracts may be provided. The foregoing method may be carried out manually, by a computer, or by a combination of manual and computerized techniques.

BRIEF DESCRIPTION OF THE DRAWINGS

In order to illustrate the above and other features of the present invention, a more particular description of the invention will be rendered by reference to specific examples thereof, which are illustrated in the appended drawings. It is appreciated that these drawings depict only typical examples of the invention and are therefore not to be considered limiting of its scope. The invention will be described and explained with additional specificity and detail through the use of the accompanying drawings in which:

FIGS. 7A and 7B are circular line plots of the peripheral regions of AFI images that illustrate the utility of specific pixel rings as test areas for illumination uniformity;

FIGS. 7C and 7D are line plots of AFI images that illustrate the utility of specific pixel rectangles as test areas for illumination uniformity;

FIGS. 8A and 8B are AFI images recorded before and after cataract surgery, respectively, for a case of a severe cataract;

FIGS. 8C and 8D are image pixel histograms corresponding to the AFI images of FIGS. 8A and 8B, respectively;

FIGS. 8E and 8F are central line plots corresponding to the AFI images of FIGS. 8A and 8B, respectively;

FIGS. 9A and 9B are AFI images recorded before and after cataract surgery, respectively, for a case with a mild cataract;

FIGS. 9C and 9D are image pixel histograms corresponding to the AFI images of FIGS. 9A and 9B, respectively;

FIGS. 9E and 9F are central line plots corresponding to the AFI images of FIGS. 9A and 9B, respectively;

FIGS. 16A through 16I show nine AFI images with associated lens opacity scores;

DETAILED DESCRIPTION

According to the invention, general AFI image evaluation criteria can be established, the status of ocular media transparence can be assessed, and/or correction factors can be developed which allow one to obtain an estimate of MPOD levels and their spatial distributions in the presence of image degradation effects due to media opacities.

Reference will now be made to the drawings to describe various aspects of the exemplary embodiments of the invention. It is to be understood that the drawings are diagrammatic and schematic representations of such exemplary embodiments, and are not limiting of the present invention. In the following description, numerous specific details are set forth in order to provide a thorough understanding of the present invention. It will be obvious however, to one skilled in the art that the present invention can be practiced without these specific details. In other instances, well-known aspects of the spectroscopy and characteristics discussed herein, the physics of light, the optical systems, and image processing procedures in general have not been described in particular detail in order to avoid unnecessarily obscuring the present invention.

Figure 1:
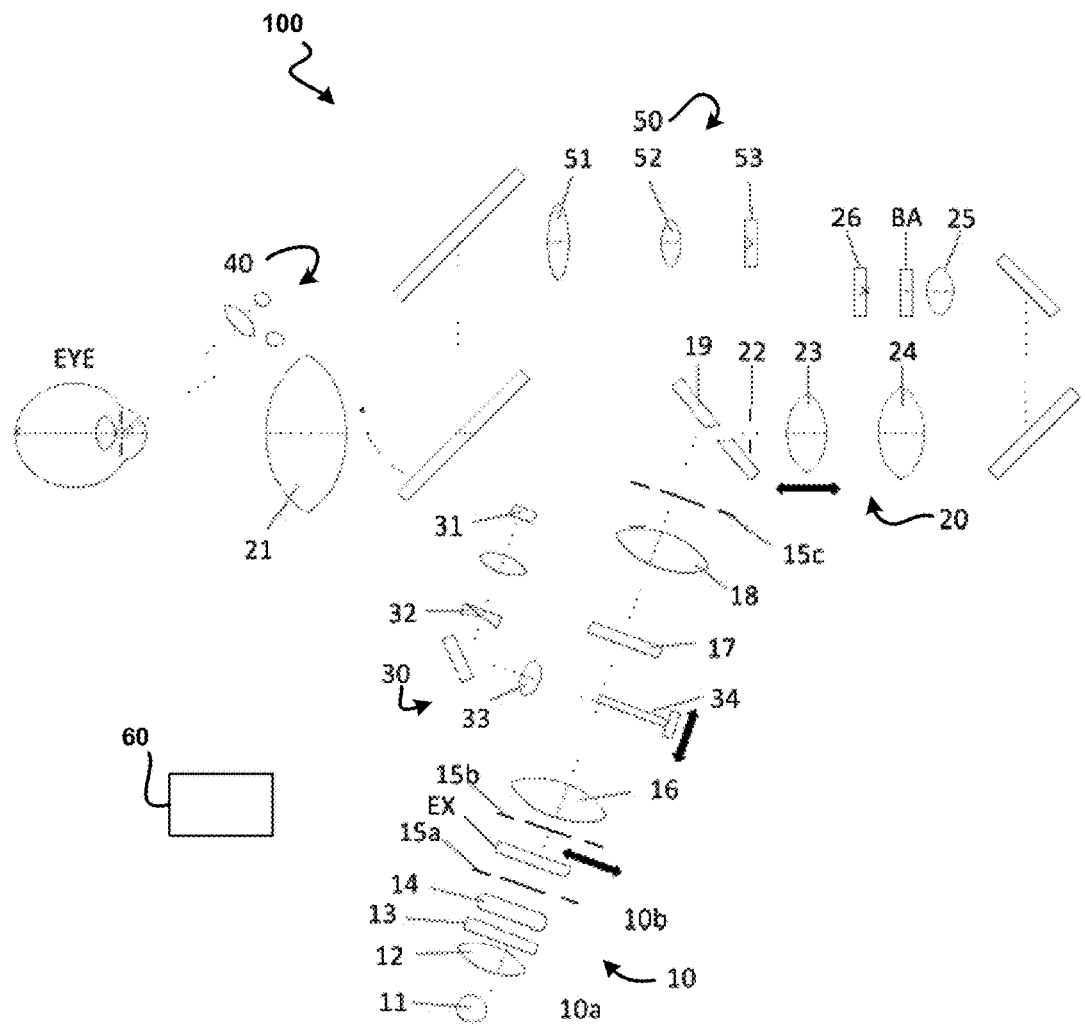
FIG. 1 is a schematic diagram of an exemplary optical system that may be used to carry out AFI imaging of MP according to one embodiment of the invention.

Referring to FIG. 1, an exemplary optical system, or optical system 100, that may be used in AFI imaging is schematically shown. The optical system 100 may optionally take the form of a modified non-mydriatic retinal/fundus camera platform for imaging of the eye. Its major optical components, according to their different functionalities, may include an optical illumination component 10, a fundus observation and image recording component 20, a focus target projection component 30, an alignment target projection component 40, and an anterior eye segment observation component 50.

The optical illumination component 10 may include an illumination component 10A and a recording component 10B. For fundus observation, the illumination component 10A may be used. The illumination component 10A may include a halogen lamp 11, a condenser lens 12, and an infrared filter 13, all of which are arranged to transmit near infrared light with wavelengths above 780 nm. Furthermore, the illumination component 10A may include ring slits 15A, 15B, and 15C, all of which may have ring-shaped openings. The illumination component 10A may further include a relay lens 16, a black dot plate 17, a relay lens 18, an aperture mirror 19, and an objective lens 21.

For recording of an AFI image, a recording component 10B is used. The recording component 10B may include a flash lamp 14 and an excitation filter EX, which may be moveable into and out of the optical path as indicated by the double-pointed arrow in FIG. 1. The recording component 10B may further include an optical system that extends from a relay lens 16 to an objective lens 21. The excitation filter EX may provide a wavelength band from about 475 to 495 nm for lipofuscin fluorescence excitation. The excitation filter EX may be removed from the optical path during fundus observation, and may be inserted into the optical path during AFI image capture.

The fundus observation and image recording component 20 may include an objective lens 21, a photographing diaphragm 22 located near an aperture mirror 19, a focusing lens 23 that is moveable along the optical axis, an image forming lens 24, a relay lens 25, and a two-dimensional imaging detector array/video camera 26 with sensitivity in the infrared wavelength region. A barrier filter BA may be positioned between the relay lens 25 and the two-dimensional imaging detector array/video camera 26 to limit the detection of lipofuscin fluorescence to the 700-850 nm infrared wavelength region.

The focus target projection component 30 may include an infrared LED light source 31, two deflection angle prisms 32 that are attached to a slit target plate, a projection lens 33, and a spot mirror 34. The spot mirror 34 may be positioned at a location conjugate with the location of the fundus. The spot mirror 34 may be removed from the optical path during photographing as shown in FIG. 1, and moved along the optical access in synchronization with the focusing lens 23. When the fundus is out of focus, the target images of the slit target plate of the deflection angle prisms 32 may be separated, and when the fundus is in focus, the target images of the slit target plate of the deflection angle prisms 32 may coincide.

The alignment target projection component 40 may project infinite and finite alignment targets onto the cornea of the subject eye. The anterior eye segment observation component 50 may include a field lens 51, a relay lens 52, and a two-dimensional image detector array 53 with sensitivity in the infrared wavelength region. It may record an image of the anterior segment of the eye illuminated by an LED light source of the alignment target projection component 40, which may emit light with a wavelength near 950 nm.

In addition to the various components described above, the optical system 100 may have, or may be connected to, a computing device 60. The computing device may receive output from the remainder of the optical system 100, and more specifically, from the two-dimensional imaging detector array/video camera 26, and may process the output in a variety of ways to accomplish tasks such as determining whether one or more cataracts are present in the lens of the eye under examination, determining whether the image can reliably indicate macular pigment content of the retina of the eye, and/or calculating a macular pigment content of the retina.

Figure 2A:
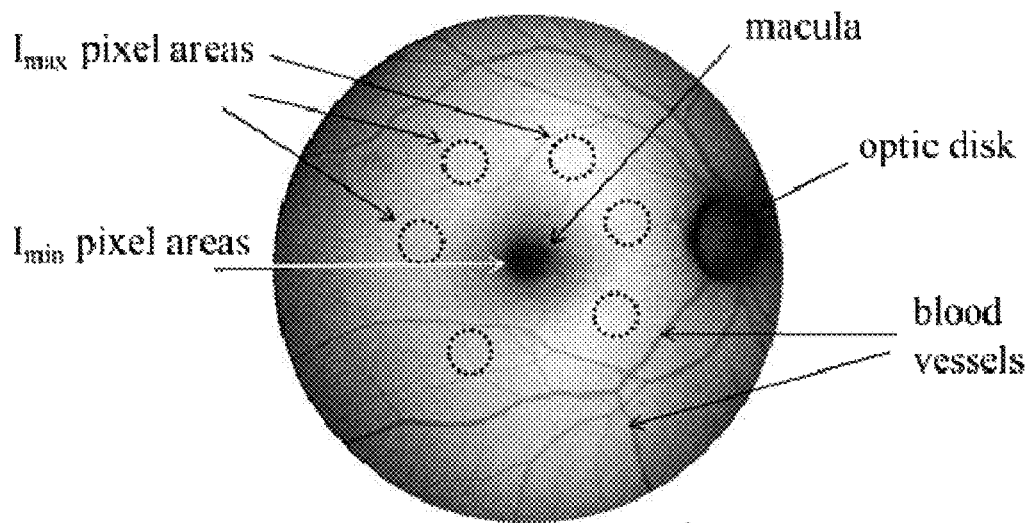
FIG. 2A is an AFI image of a subject eye with clear ocular media, showing key image features of interest, illustrating the image processing concept.
Figure 2B:
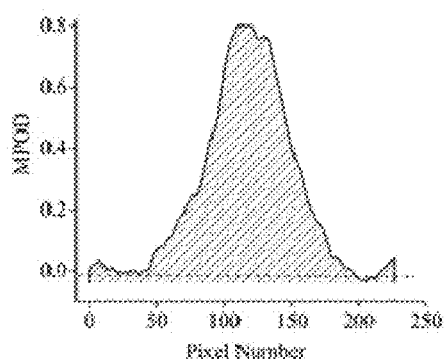
FIGS. 2B and 2C are a two-dimensional line plot and three-dimensional spatial MPOD distribution, respectively, that illustrate MP results derived from the image of FIG. 2A.
Figure 2C:
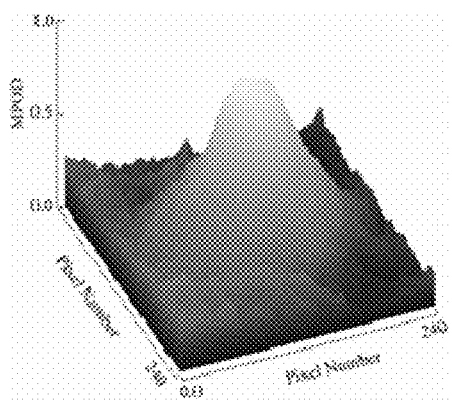

Referring to FIGS. 2A through 2C, an AFI image (FIG. 2A) of a subject eye with clear ocular media is shown, along with image processing that may be used to derive quantitative information for the MPOD level across the macula of the retina of the eye. The quantitative information may be derived through the use of a line plot of MPOD levels through the center of the macula (FIG. 2B) and/or through the use of a spatial distribution of MPOD levels (FIG. 2C). Also, subject-specific MPOD levels may be presented as peak MPOD levels in the center of the line plot/center of the MPOD distribution, or as MPOD volume under the distribution.

In the raw AFI image of FIG. 2A, the MP may be seen as a heavily attenuated fluorescence region, i.e., a dark region, in the center of the image. Also, retinal blood vessels may be seen in the vicinity of the macula and the optic disc may be seen near the edge of the image, with all corresponding image/pixel areas featuring heavily attenuated fluorescence intensities.

The AFI image in FIG. 2 is well centered on the macula, it is in focus, and the illumination is uniform, as evidenced, respectively, by clearly resolved dark blood vessels and by the evenly high lipofuscin fluorescence intensities surrounding the macular area. The high intensities may appear as bright, ring-shaped, image regions. For the derivation of quantitative MPOD characteristics from the image pixel intensity map, circular pixel areas (outlined by dotted circles) may be chosen in the vicinity of the macula at about 7° eccentricity, and at image/tissue locations that are free of blood vessels. These pixel areas with their associated intensities are labeled as $I_{max}$. Similarly, much smaller circular pixel areas may be chosen within the attenuated fluorescence intensity region of the macula (not shown), labeled as $I_{min}$.

The MPOD levels for the small pixel areas within the macula may be calculated as the negative logarithm of the ratio between $I_{min}$ and the average of the various $I_{max}$ intensities, $I_{max(ave)}$. A multiplication factor of 1.4 may be used to take into account the spectral overlap of the excitation light spectrum with the macular pigment absorption band for the instrument platform used to generate the AFI image (for example, the optical system 100 of FIG. 1). The explicit mathematical expression for the calculation of the optical density levels of MP at any pixel area $I_{min}$ within the macular region may be given by:

$$OD = -1.4 \log \{I_{min}/I_{max(ave)}\}.$$

As indicated by the MPOD line plot and spatial distribution in FIG. 2B, the highest MPOD level is 0.8 for this subject's retina, and it occurs within a nearly circularly symmetrical distribution. The line plot of FIG. 2B may be taken by plotting the pixel intensities along a line extending generally medial-laterally through the macula of the AFI image, i.e., along a nasal-temporal meridian. The pixel intensities of the AFI image as a whole may be plotted in three dimensions and may be used to access the distribution of macular pigment across the entire AFI image. FIG. 2C illustrates the substantially radial symmetry of the distribution of MPOD intensity in the AFI image of FIG. 2A, in a three-dimensional format.

The nominal MPOD levels derivable from AFI images may be largely dependent on the achievable image contrast, i.e., the ratio between lipofuscin intensities in the macular region of the image and intensities in the periphery. For meaningful image processing, it may be advantageous to establish a number of image quality criteria relating to general image characteristics, to determine the status of ocular media transparency, and, if such of media opacities are not too severe for MPOD to be derived from the AFI image, to derive corrected MPOD estimates.

More specifically, it may be advantageous to provide one or more image acceptance criteria and one or more image clarity criteria, and to apply both sets of criteria to the AFI image to accomplish the foregoing. The image acceptance criteria may be designed to determine whether the AFI image was properly taken; if they are not met, the AFI image may be re-taken. The image acceptance criteria may include proper centering of the macula, image focusing, and/or illumination of the eye. These image acceptance criteria are merely exemplary; other image acceptance criteria may be used in addition to or in the alternative to those listed above. The exemplary image acceptance criteria will be shown and described in connection with FIG. 4 for proper centering of the macula, FIG. 5 for proper image focusing, and FIGS. 6 through 7D for proper illumination of the eye.

If the AFI image meets the image acceptance criteria, the image clarity criteria may be applied to determine whether the AFI image is sufficiently clear to provide an indication of the macular pigment level, diagnose the presence and/or severity of cataracts in the eye, and/or determine whether and/or how much the reported macular pigment level should be adjusted based on the presence of such cataracts. The image clarity criteria may include a determination of whether a histogram for the AFI image is acceptable and/or a determination of whether the blood vessel contrast visible in the AFI image is acceptable. These image clarity criteria are merely exemplary; other image clarity criteria may be used in addition to or in the alternative to those listed above. The exemplary image clarity criteria will be shown and described in connection with FIGS. 8A through 9F for histogram analysis, and FIGS. 12A and 12B for blood vessel contrast analysis.

Figure 3:
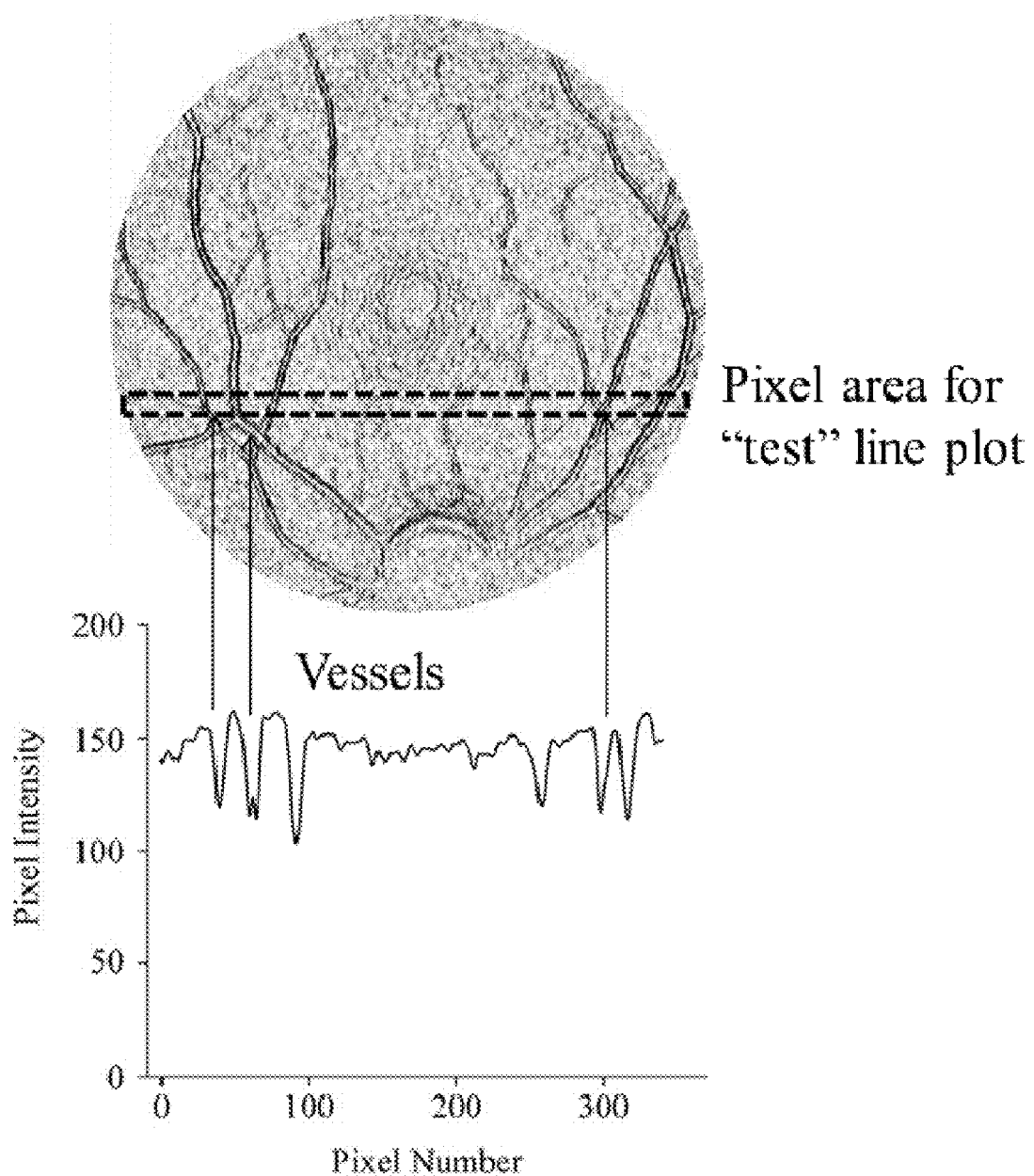
FIG. 3 is an AFI image and test pixel area that illustrate the use of image pixel areas and related line plots for the quantification of blood vessel contrast.

Referring to FIG. 3, an AFI image and test pixel area illustrate the use of image pixel areas and related line plots for the quantification of blood vessel contrast. Retinal blood vessels may be used as an indicator of acceptable image quality. The concept is illustrated in FIG. 3, where a rectangular test pixel area, outlined in dashed lines, is shown superimposed on an AFI image. The test pixel area may run across the image in a peripheral retinal area and may cross numerous blood vessels. Since the blood vessels strongly absorb the blue excitation light, they appear as sharp, pronounced dips in the corresponding line plot of the fluorescence intensities.

In FIG. 3, the test pixel area may run in the medial-lateral direction, but may not intersect the macula. In addition to or in the alternative to the use of such a pixel test area, a line plot may be based on a pixel test area that runs across a central area of the AFI image, including the macular area. In an acceptable AFI image, the intensities along such a line plot may be well-attenuated in the central region/MP area relative to the peripheral regions.

Additionally or alternatively, histograms may be calculated for pixel intensity maps of a part of the AFI image or of the whole AFI image. In an acceptable AFI image, the corresponding pixel histogram may show considerable width when plotting the number of pixels with identical intensity versus intensities; in an image blurred by media opacities, the corresponding image histogram may sharply peak at the intensity values that occur most frequently in the blurred image.

Figure 4A:
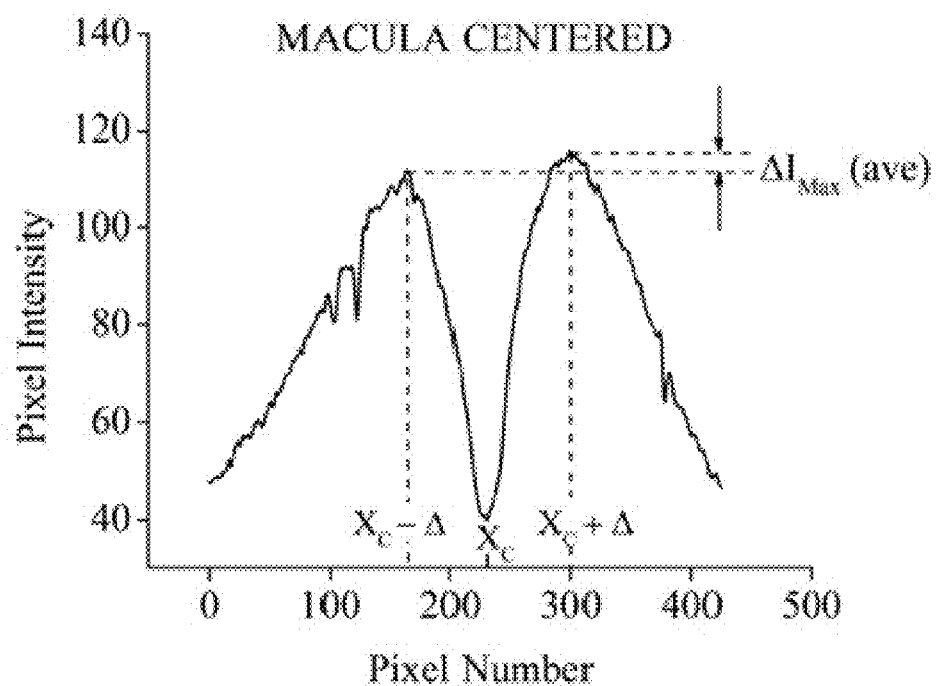
FIGS. 4A and 4B are line plots that illustrate the importance of centering of the macula in the AFI image in relation to the characteristics of resulting line plots running through the macular region.
Figure 4B:
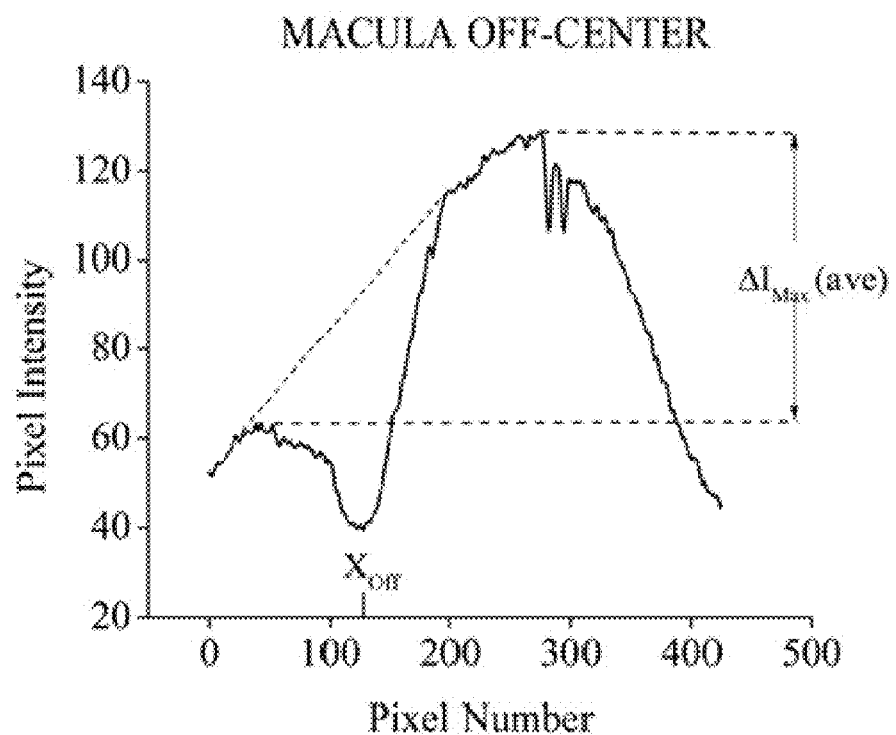

Referring to FIGS. 4A and 4B, line plots illustrate the importance of centering of the macula in the AFI image in relation to the characteristics of resulting line plots running through the macular region. In an AFI image that is centered on the macula, as in FIG. 4A, the corresponding central line plot may be generally symmetrical, and may display a pronounced dip of the pixel intensities in the center of the image, with the depth of the dip correlating with the strength of the MP absorption at the macula. For the particular AFI image that was processed to generate FIG. 4A, this dip occurs near pixel number 220, marked as $X_C$. Pixel intensities rise on either side of the macula towards more peripheral pixels, reaching maxima at pixel locations $X_C \pm \Delta$, and the intensities decrease again towards further peripheral pixels. Blood vessels may be seen as pronounced dips outside the macular area in the 130 and 370 pixel number range, respectively. The MPOD level in the center of the macula may be calculated as 0.6 for this centered image using the formula presented earlier.

For an AFI image with the macula in an off-center position, shown in FIG. 4B, the corresponding central line plot may asymmetrical, with strongly differing pixel intensities on either side of the center of the macula, which now lies in the 120 pixel number region marked as $X_{Off}$. The MPOD level in the center of the macula for this off-center image may be calculated as 0.4 using the formula presented above. These different MPOD results may be a consequence of the excitation light varying in intensity across the image in the fundus camera platform, and thus also varying across the macular area when off-center. For acceptable AFI images, it may therefore be advantageous to require the macula to be positioned in the image center to within a predetermined deviation limit, and also to be illuminated relatively uniformly. Alternatively, if the eccentricity is not too large, it may be possible to multiply the nominal MPOD level obtained at the eccentric, non-centered, region by an appropriate correction factor (1.5 in this case).

Figure 5:
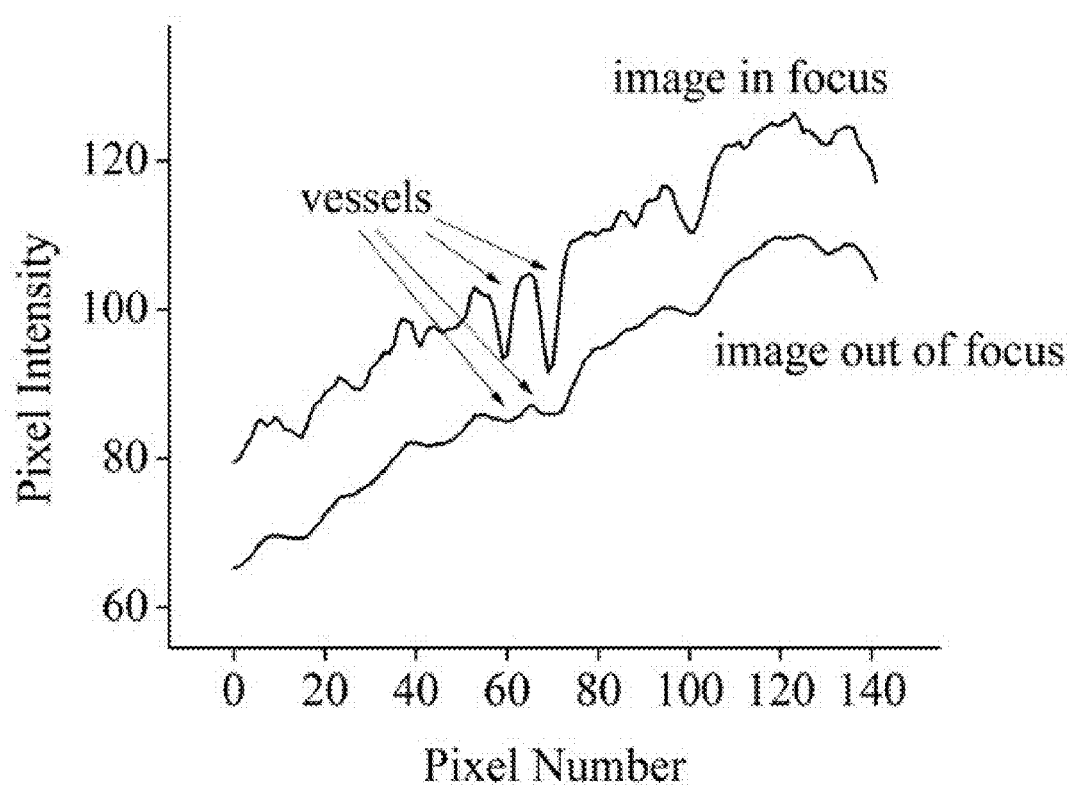
FIG. 5 is a pair of superimposed line plots that illustrate the importance of focusing of the retina in relation to achievable blood vessel contrast in the vicinity of the macula.

Referring to FIG. 5, a pair of superimposed line plots illustrate the importance of focusing of the retina in relation to achievable blood vessel contrast in the vicinity of the macula. In FIG. 5, imaging effects are investigated in relation to proper focusing of the optics on the retina. In a sharply-focused AFI image, the blood vessels may be easily identifiable in line plots running across the image as sharp intensity dips at specific pixel locations, as in the upper plot. In poorly-focused images, as in the lower line plot, the blood vessels may be represented as only degraded intensity modulations in the vessel regions. In a poorly-focused AFI image, the signature of the blood vessels in the corresponding line plot may effectively be washed out.

As a quantitative criterion for proper focusing, one can choose a suitable intensity modulation threshold in the blood vessel regions. Additionally or alternatively, a limit for the pixel widths of the vessels may be chosen; in un-focused AFI images, such a pixel width may be broader than in focused AFI images.

Figure 6:
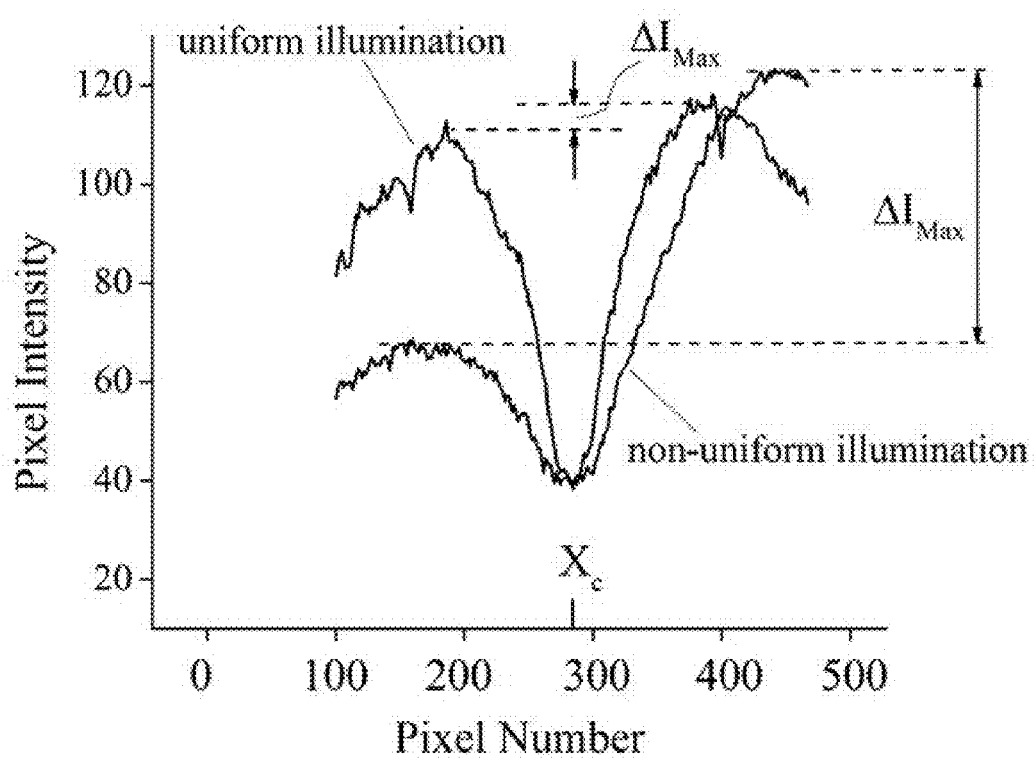
FIG. 6 is a pair of superimposed line plots that illustrate the effect of illumination non-uniformity in AFI images in relation to the characteristics of resulting line plots running through the vicinity of the macular region.

Referring to FIG. 6, a pair of superimposed line plots illustrate the effect of illumination non-uniformity in AFI images in relation to the characteristics of resulting line plots running through the vicinity of the macular region. In FIG. 6, illumination non-uniformities of the retina are illustrated in relation to their effects on a circularly symmetric MPOD distribution. Under uniform illumination, i.e., with the macular region uniformly illuminated as shown in FIG. 2A, a central line plot for the MP distribution may be generally symmetrical in terms of pixel intensities on either side of the central intensity dip, leading to small differences in $I_{max}$ intensities of the various peripheral reference areas. Under non-uniform illumination conditions, the intensity dip may still occur at the same central pixel location (assuming the same centering of the AFI image), but the intensities may increase asymmetrically with increasing eccentricities, leading to large differences in $I_{max}$ intensities.

A proper quantitative criterion for proper illumination of the retina may relate to the size of the difference between $I_{max}$ intensities (i.e., $\Delta I_{max}$) on either side of the portion of the line plot that represents the macular region. In general, the shape of the MP distributions may not be known a priori. The MP distribution could be asymmetric or fragmented. It may be preferable, therefore, in establishing a suitable criterion for uniform illumination, not to involve any MP features. A more general criterion can be established, instead, by requiring that a ring-shaped pixel test area surrounding the center of the pixel array, with an eccentricity just high enough to lie outside the MP region, for example at 7° eccentricity, have a constant intensity along its rim to within a pre-determined limit. Also, the corresponding pixel intensity histogram could be required to have a sharp profile to within a predetermined intensity variation limit. Similarly, a line plot running across the AFI pixel map just outside the macular region may be required to have a symmetrically shaped intensity profile that correlates with the known parabolic illumination intensity profile of the instrument across the image, with the apex of the parabola positioned in the center of the line plot, to within a pre-determined limit.

Referring to FIGS. 7A and 7B, circular line plots of the peripheral regions of AFI images illustrate the utility of specific pixel rings as test areas for illumination uniformity. FIG. 7A illustrates the pixel intensities in the peripheral regions of a non-uniformly illuminated AFI image. FIG. 7B illustrates the pixel intensities in the peripheral regions of a uniformly illuminated AFI image. As shown, the consistency of pixel intensity in the circular line plot of FIG. 7B is much greater than in FIG. 7A. Thus, a quantitative criterion for proper illumination of an AFI image may be based on the variation in intensity present in a circular line plot such as those of FIGS. 7A and 7B. Such a quantitative criterion may involve a maximum standard deviation or variation level above which the AFI image is assumed to be improperly illuminated.

Referring to FIGS. 7C and 7D, line plots of AFI images illustrate the utility of specific pixel rectangles as test areas for illumination uniformity. FIG. 7C is a line plot running across the AFI pixel map used to generate FIG. 7A, just outside the macular region. Similarly, FIG. 7D is a line plot running across the AFI pixel map used to generate FIG. 7B. As shown, the pixels at the left and right ends of the line plot of FIG. 7D both have a low intensity value. However, in FIG. 7C, the pixels at the left-hand end of the line plot have a mid-range intensity value, illustrating that the corresponding end of the AFI image may have been overly-illuminated. Thus, a quantitative criterion may involve a maximum intensity of pixels at either end of such a line plot; if the pixel intensity at either end of the line plot exceeds the threshold, the AFI image may be assumed to be improperly illuminated.

Media opacities of ocular media anterior to the retina can be expected to degrade the image contrast achievable in AFI images in the macula area as well as in the peripheral retina. This is due to the combined scattering and absorption effects caused by the respective opacities. Anterior optical media include the cornea, the aqueous humor, the lens, and the vitreous humor. The strongest opacity effect can be expected from cataracts, often forming in human eyes with increasing age.

To investigate the quantitative effect of cataracts on the nominal MPOD levels derivable from AFI images, a clinical trial was conducted that involved AFI imaging of a large subject population measured before and after cataract surgery. The population included 93 subjects aged 22-87 years (34 males, 59 females). The mean age was 72.0±11.6 years. AFI images were obtained for 140 eyes.

Referring to FIGS. 8A through 8F, AFI images, histograms, and center line plots illustrate the difference in clarity, and related analytical tools, for an eye imaged before and after cataract surgery. More specifically, in FIGS. 8A and 8B, AFI images are shown as recorded before and after cataract surgery, respectively, for a case of a severe cataract. In FIGS. 8C and 8D, image pixel histograms are shown for the AFI images of FIGS. 8A and 8B, respectively. In FIGS. 8E and 8F, central line plots are shown for the AFI images of FIGS. 8A and 8B, respectively.

The effects of cataracts on obtainable AFI image quality are illustrated for a relatively severe cataract case, with LOCS III scores of 4, 3, and 4, for nuclear, cortical, and posterior sub-capsular lens opacities, respectively. Before cataract surgery of the patient, blood vessels and other landmark features are severely washed out in the AFI image of FIG. 8A, leading to a corresponding sharply peaked pixel histogram, as shown in FIG. 8C. The peak may occur near pixel intensity 150, and the histogram may have a narrow full width encompassing only about 15% of the possible intensity values. Furthermore, the central line plot of pixel intensities, as shown in FIG. 8E, shows only a negligible modulation. It may not be possible to derive a nominal MPOD level from this image.

After cataract surgery, a high quality AFI image is obtained from the same subject, as shown in FIG. 8B, with the MP showing up as a strongly attenuated central region, and with blood vessels and optic disk now clearly resolved. The associated pixel histogram shown in FIG. 8D is much wider, has a substructure, and it has more pixels with lower intensities, by comparison with the histogram of FIG. 8C. This leads to a shift of the center of the histogram by approximately 50 to a lower pixel intensity of about 100. The width of the distribution of intensities shown in the histogram may have a broad width encompassing about 80% of the possible intensity values. In FIG. 8F, the central line plot across the image shows a strong modulation of pixel intensities with a fluorescence intensity difference of about 90 between the center of the MP dip, which has an intensity of about 50, and the peripheral reference, which has an intensity of about 140.

Referring to FIGS. 9A through 9F, AFI images, histograms, and center line plots illustrate the difference in clarity, and related analytical tools, for an eye imaged before and after cataract surgery. More specifically, in FIGS. 9A and 9B, AFI images are shown as recorded before and after cataract surgery, respectively, for a case of a mild cataract. In FIGS. 9C and 9D, image pixel histograms are shown for the AFI images of FIGS. 9A and 9B, respectively. In FIGS. 9E and 9F, central line plots are shown for the AFI images of FIGS. 9A and 9B, respectively.

In FIG. 9A, the effects of cataracts on obtainable AFI image quality are illustrated for a less severe cataract case, with MP recognizable as a faint shading of the central image area. By comparison with the histogram in FIG. 8C for the severe cataract AFI image of FIG. 8A, the associated pixel intensity histogram in FIG. 9C is slightly wider at half maximum (about 18%) and much wider at the base, and a central line plot shows a modulation of about 20 that is well recognizable above the background noise levels. Before surgery, it is possible to determine a nominal MPOD level for the blurred image. This MPOD may advantageously be adjusted based on the clarity of the AFI image to provide an approximation of the MPOD level within the eye.

After cataract surgery, a high quality image may again be obtained from this subject's retina, with the MP showing up again as a strongly attenuated central region, and with blood vessels and optic disk again clearly resolved, as shown in FIG. 9B. The associated pixel histogram is again much wider (about 100%), has a substructure, and is shifted again to lower intensities. A central line plot across the image shows a strong modulation of pixel intensities with a fluorescence intensity difference of about 55 between the center of the MP dip (about 40) and the peripheral reference (about 95).

Similar comparisons of AFI images recorded for a large population before and after cataract surgery may allow one to establish a high power statistical correlation between the MPOD levels determined before and after surgery. Such data may provide a basis for opacity-corrected MPOD level estimates to within certain limits of confidence.

Figure 10:
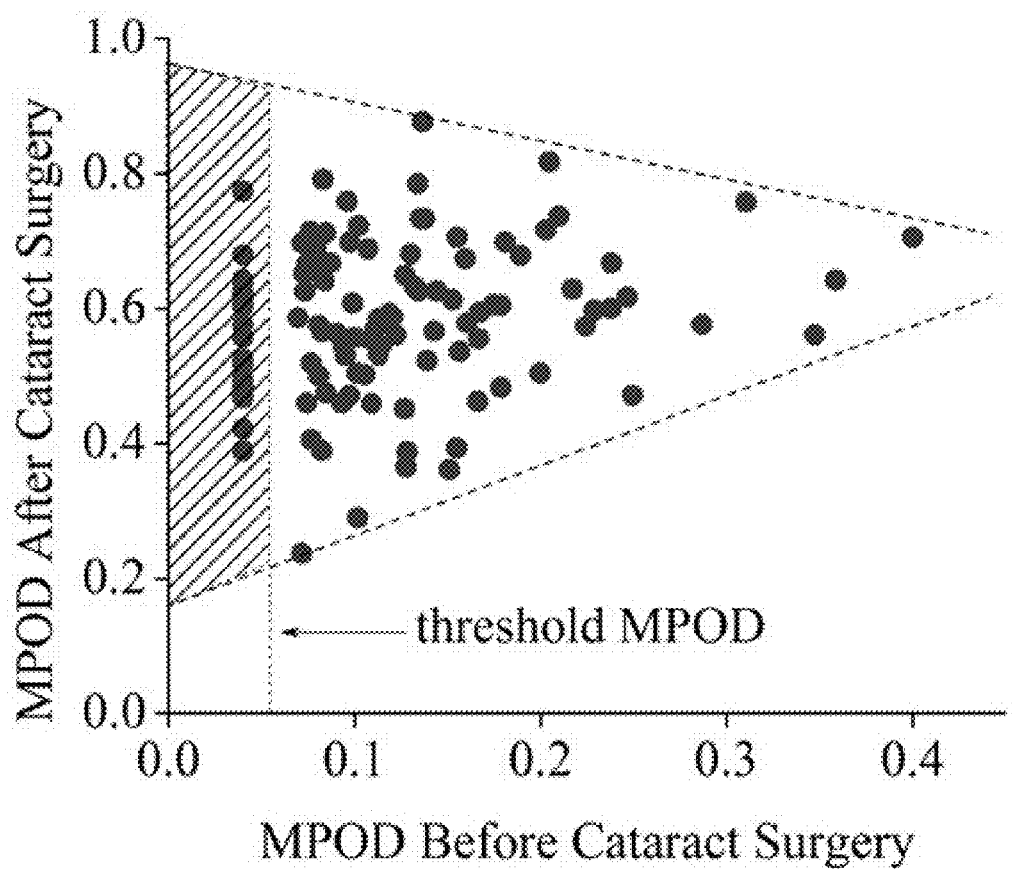
FIG. 10 is a plot showing MPOD levels for 74 subject eyes measured before and after cataract surgery, respectively.

Referring to FIG. 10, a plot shows MPOD levels for 129 subject eyes measured before and after cataract surgery, respectively. Data points for some of the subject eyes overlap, so the number of data points shown in FIG. 10 is smaller than the number of subjects measured. In FIG. 10, the MPOD levels in the center of the recorded pixel intensity distributions are shown for all eyes for which AFI images with acceptable quality could be obtained before and after surgery (74 eyes), and for additional eyes for which MPOD levels could be obtained only after cataract surgery (55). As a criterion for image processability, a pre-surgery threshold image contrast was chosen corresponding to an MPOD limit of 0.08. All images with a contrast below that threshold were counted as having a nominal MPOD limit of 0.04. In FIG. 10, the MPOD levels obtained for all those eyes after surgery are therefore lying on a vertical line in the plot, with a common pre-surgery MPOD level of 0.04.

Accordingly, nominal pre-surgery MPOD levels vary between about 0.04 and 0.4, with a majority of subjects having nominally low MPOD levels below 0.2. Only a small number of eyes (13) have nominal MPOD levels above 0.2. Post-surgery levels vary between 0.25 and 0.87, with a large variation for low pre-surgery levels and smaller variation at higher levels. This may be due to the fact that less severe cataracts may lead to less severe blurring and/or illumination scattering, which may cause such eyes to show relatively high pre-surgery MPOD levels in comparison with eyes that have more severe cataracts.

This may lead to the triangular boundaries shown by the dashed lines at the top and bottom of the plot. As examples, nominal pre-surgery MPOD levels in the 0.3 range are only reduced by a factor of about 2 relative to their post-surgery levels of 0.6, whereas levels in the 0.15 range are reduced by an average factor of about 4. These trends can be used to generate a formula, lookup table, or other system whereby an adjustment factor may be provided. The adjustment factor may be applied to a pre-operative MPOD measurement to yield the likely actual macular pigment content of the retina that would probably be observed if the eye is re-imaged after cataract surgery. This actual MPOD level may be the most useful for diagnosing the presence and/or prevalence of macular degeneration in a manner that remains accurate even when the eye also has one or more cataracts.

Figure 11A:
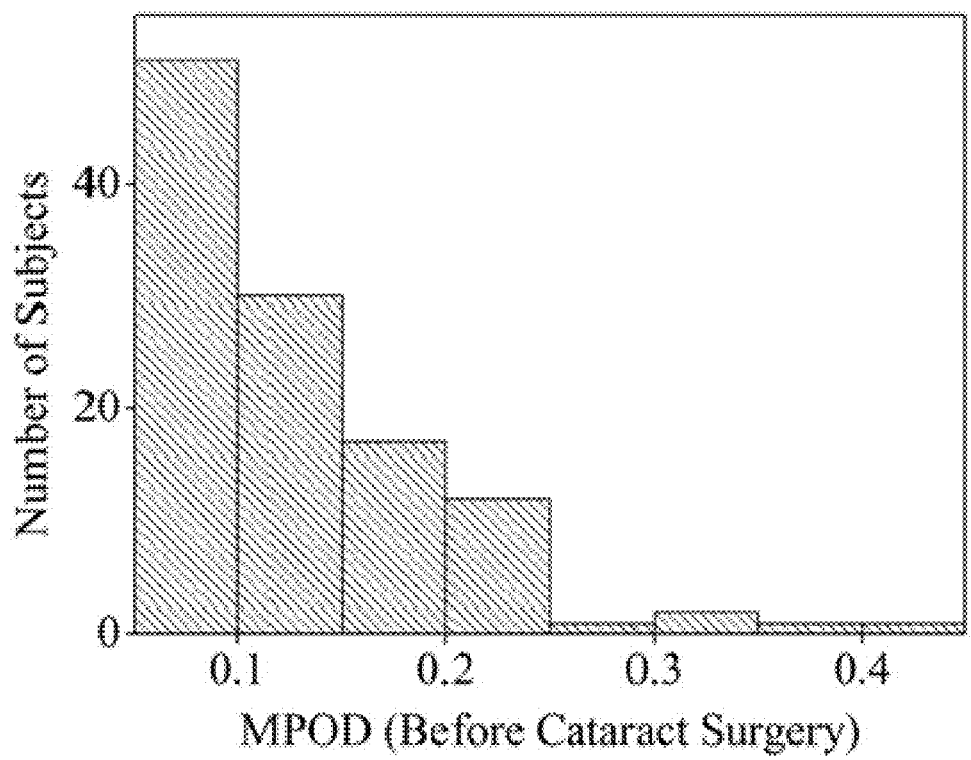
FIGS. 11A and 11B are histograms of the MPOD levels for all 140 subject eyes, measured before and after cataract surgery, respectively.
Figure 11B:
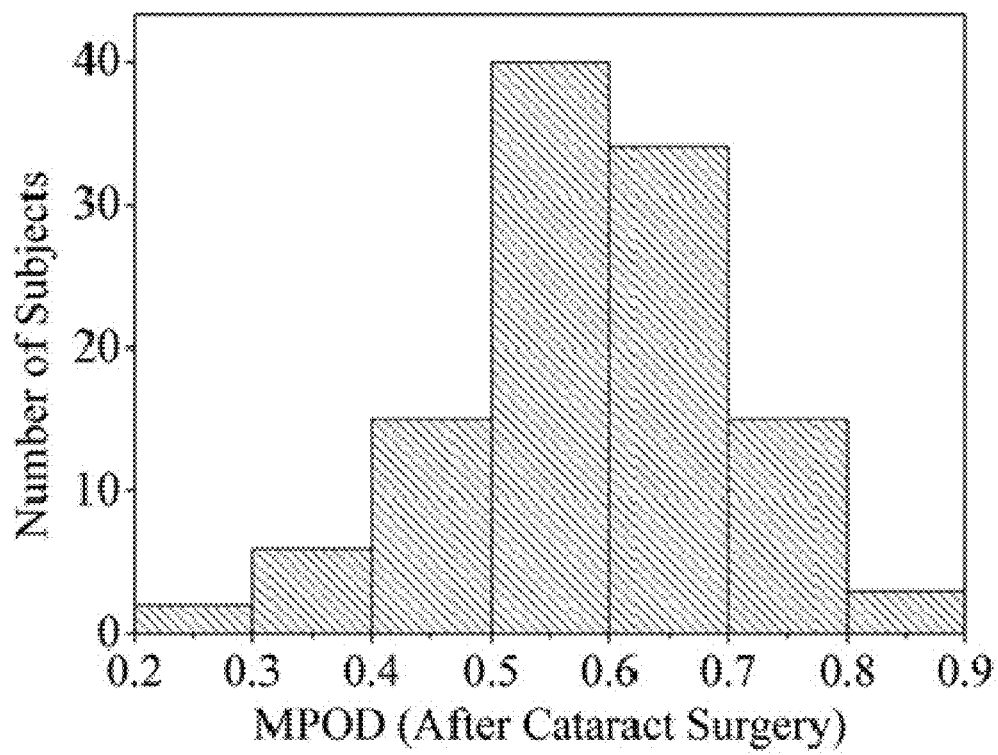

Referring to FIGS. 11A and 11B, histograms illustrate the MPOD levels for all 129 subject eyes, measured before and after cataract surgery, respectively. The post-surgery histogram of FIG. 11B has a nearly bell-shaped envelope and shows that in the highest number of eyes an MPOD level of about 0.6 is present. The pre-surgery histogram of FIG. 11A has an approximately exponentially decreasing envelope.

In order to develop a predictor for MPOD levels in the presence of media opacities pre-surgery, the contrast of blood vessels derived from lipofuscin fluorescence intensities prior to cataract surgery was also compared with that found after cataract surgery. These comparisons included comparisons of AFI image features and AFI image histograms.

Figure 12A:
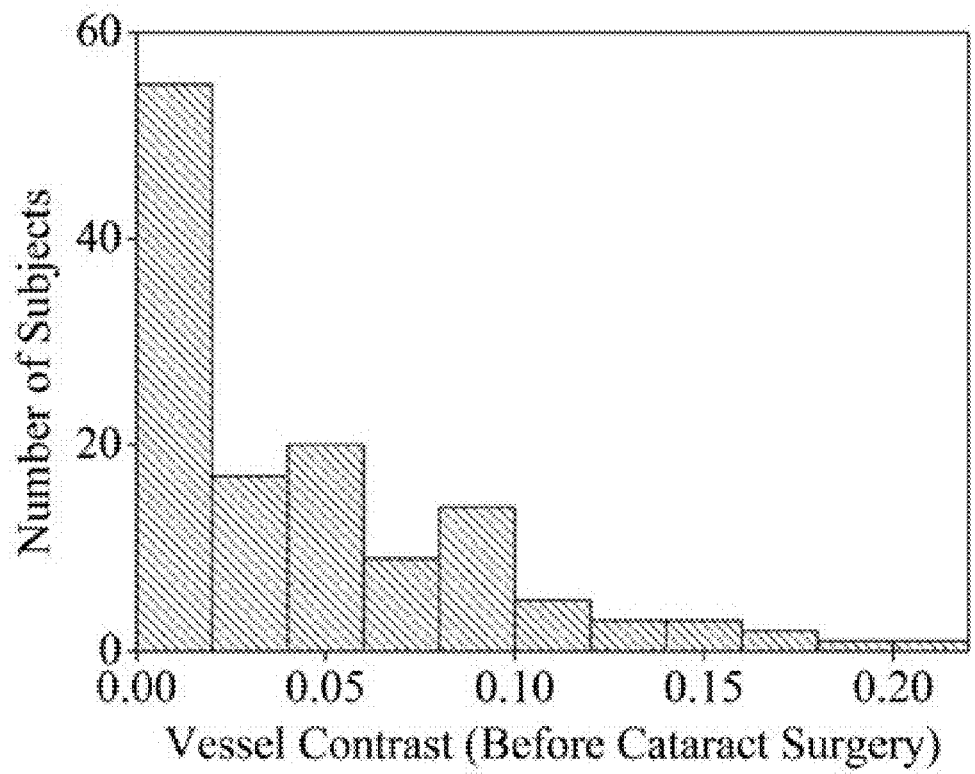
FIGS. 12A and 12B are histograms illustrating blood vessel contrast for all 140 subject eyes, measured before and after cataract surgery, respectively.
Figure 12B:
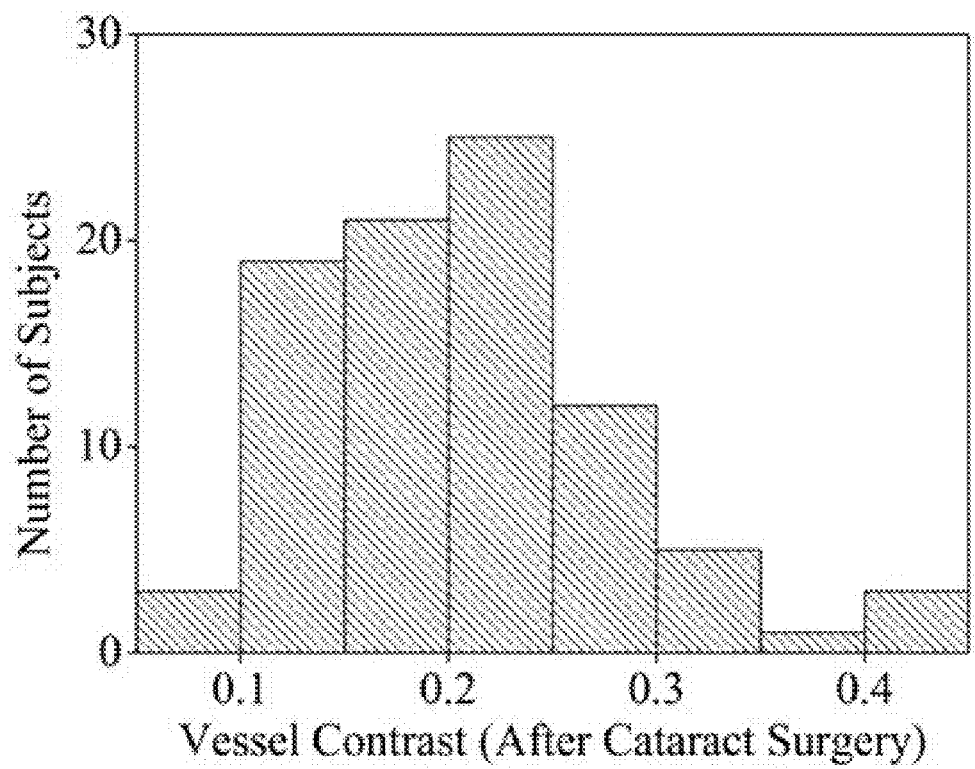

Referring to FIGS. 12A and 12B, histograms illustrate blood vessel contrast for all 129 subject eyes, measured before and after cataract surgery, respectively. Before surgery, the vessel contrast values are small, as shown in FIG. 12A. The pre-surgery contrast values vary from essentially non-existing for the majority of eyes, with values in the 0 to 0.05 range, to contrasts up to about 0.20, with a decreasing exponential envelope. After cataract surgery, the vessel contrasts for all eyes have a bell-shaped envelope, as shown in FIG. 12B. The post-surgery contrast values peak at a contrast value of about 0.2, which may be taken for the average contrast value for an eye without cataracts.

In any given AFI image pre-surgery, the deviation of the observed blood vessel contrast value from the unobstructed mean value of 0.2 can be used as a criterion for the severity of the scattering, and thence, the severity of the cataract. Accordingly, histograms and/or average blood vessel contrast values like those of FIGS. 12A and 12B can be processed to determine whether an image clarity criterion regarding blood vessel contrast has been met. The further the contrast level is below the 0.2 average unobstructed contrast level, the more severe the cataracts in the eye are likely to be, and the more the measured MPOD levels from the AFI image will need to be scaled up to remove the effect of the cataracts.

Figure 13A:
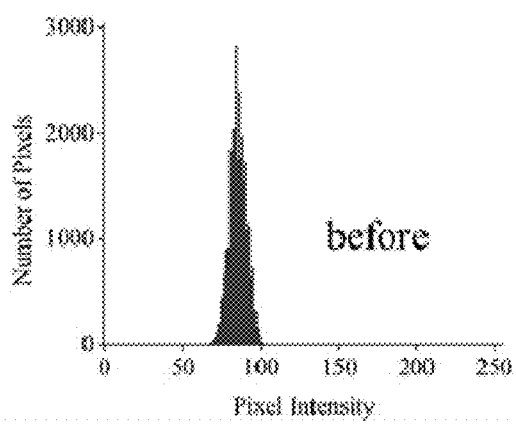
FIGS. 13A and 13B show pixel intensity histogram characteristics of AFI images obtained for two subjects with strong and weak cataract, respectively, prior to cataract surgery.
Figure 13B:
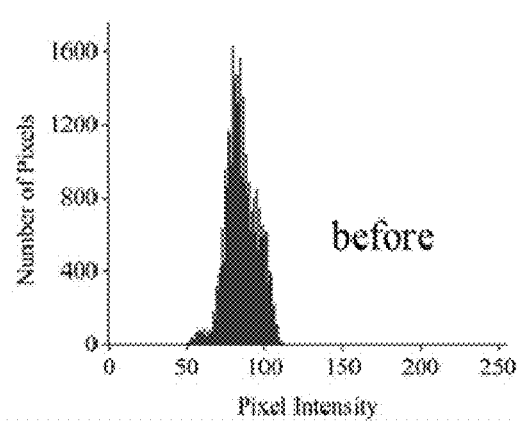
Figure 13C:
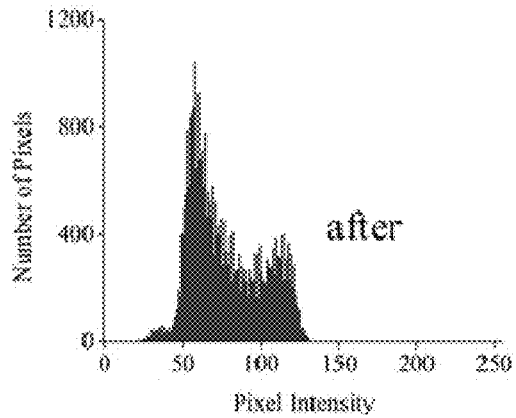
FIGS. 13C and 13D show pixel intensity histogram characteristics of AFI images obtained for the two subjects of FIGS. 13A and 13B, respectively, after cataract surgery.
Figure 13D:
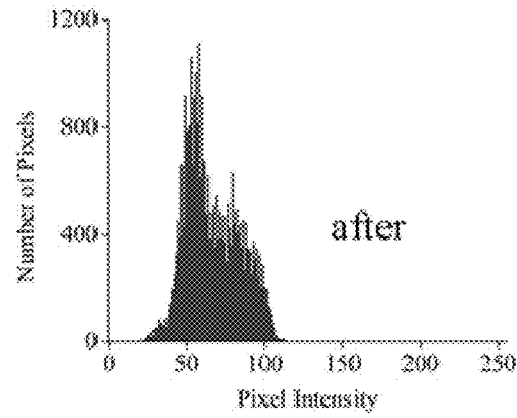

Referring to FIGS. 13A through 13D, a series of pixel intensity histograms illustrate further characteristics of histograms associated with blurred AFI images obtained pre-surgery relative to AFI images recorded after surgery. More specifically, FIGS. 13A and 13B show pixel intensity histogram characteristics of AFI images obtained for two subjects with strong and weak cataract, respectively, prior to cataract surgery. FIGS. 13C and 13D show pixel intensity histogram characteristics of AFI images obtained for the two subjects of FIGS. 13A and 13B, respectively, after cataract surgery.

In FIGS. 13A through 13D, the effects on the scattering are shown on the shape of the histograms derived from a pixel area that specifically excludes the area of the optic disk. This can be achieved by defining a circular pixel area, centered on the macula, with a radius corresponding to an eccentricity that is lower than the eccentricity to the edge of the optic disk. Using a suitable eccentricity of about 7°, which lies roughly in the middle between the center of the macula and the edge of the optic disk, the effects of scattering are shown for the two sets of pre- and post-surgery histograms.

In FIGS. 13A and 13C, the pixel intensity histograms show results from AFI images of a subject eye with a low nominal MPOD level of about 0.14 pre-surgery and an MPOD level of 0.78 post-surgery ("Subject 1"). Due to strong scattering, the pre-surgery pixel intensity width at base is relatively narrow, ranging from pixel intensities 70-100, while the post-surgery levels, obtained through clear ocular media, range from about 25-130.

In FIGS. 13B and 13D, a subject eye having a nominal MPOD level of 0.35 ("Subject 2"), the pre-surgery intensity range extends from 50-115. Post-surgery, the MPOD level is 0.64, and the post-surgery histogram width at base extends from about 25-115. A comparison of the base histogram widths for the two subjects reveals that the histogram widths at base may be indicative of the degree of scattering existing prior to surgery, i.e. small width may indicate stronger scattering than large width.

In order to derive histogram-related correction factors for the nominal MPOD levels derived from pre-surgery AFI images, the ratio of MPOD levels before and after surgery for each subject may be plotted versus the histogram base width pre-surgery. Such a plot will be shown and described in connection with FIG. 14.

Figure 14:
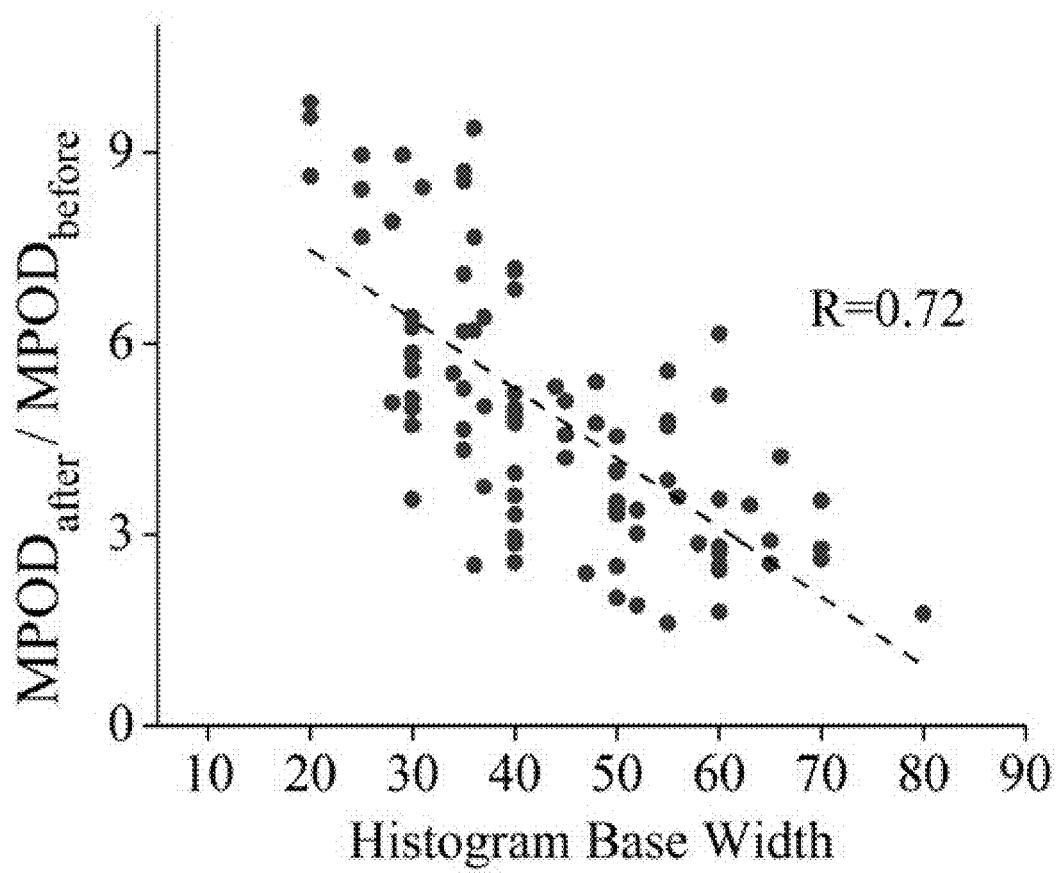
FIG. 14 is a plot of MPOD ratios for 74 subjects illustrating ratios between post- and pre-surgery MPOD levels, versus base width of pixel intensity histogram of pre-surgery AFI image.

Referring to FIG. 14, a plot of MPOD ratios for 74 subjects illustrates ratios between post- and pre-surgery MPOD levels, versus base width of pixel intensity histogram of pre-surgery AFI image. On average, the plot shows a clear, generally linear, decline of the MPOD ratios with increasing base width, meaning that for small base widths of the pre-surgery histograms, the ratios differ by a large factor (up to about 9), and that for large base widths pre-surgery, the ratio is converging to a small factor (about 2).

The plot may allow the correction of pre-surgery MPOD levels with a histogram-specific correction factor. In other words, true MPOD levels may be predicted with high confidence even in the presence of cataracts, as long as a minimum threshold MPOD level is observable in the pre-surgery AFI images. The histogram base width may be used to obtain the appropriate correction factor to apply to an AFI image to correct for the presence of cataracts in the eye. The applicable correction factor may be the $MPOD_{after}/MPOD_{before}$ ratio shown on the vertical axis of FIG. 14.

Figure 15:
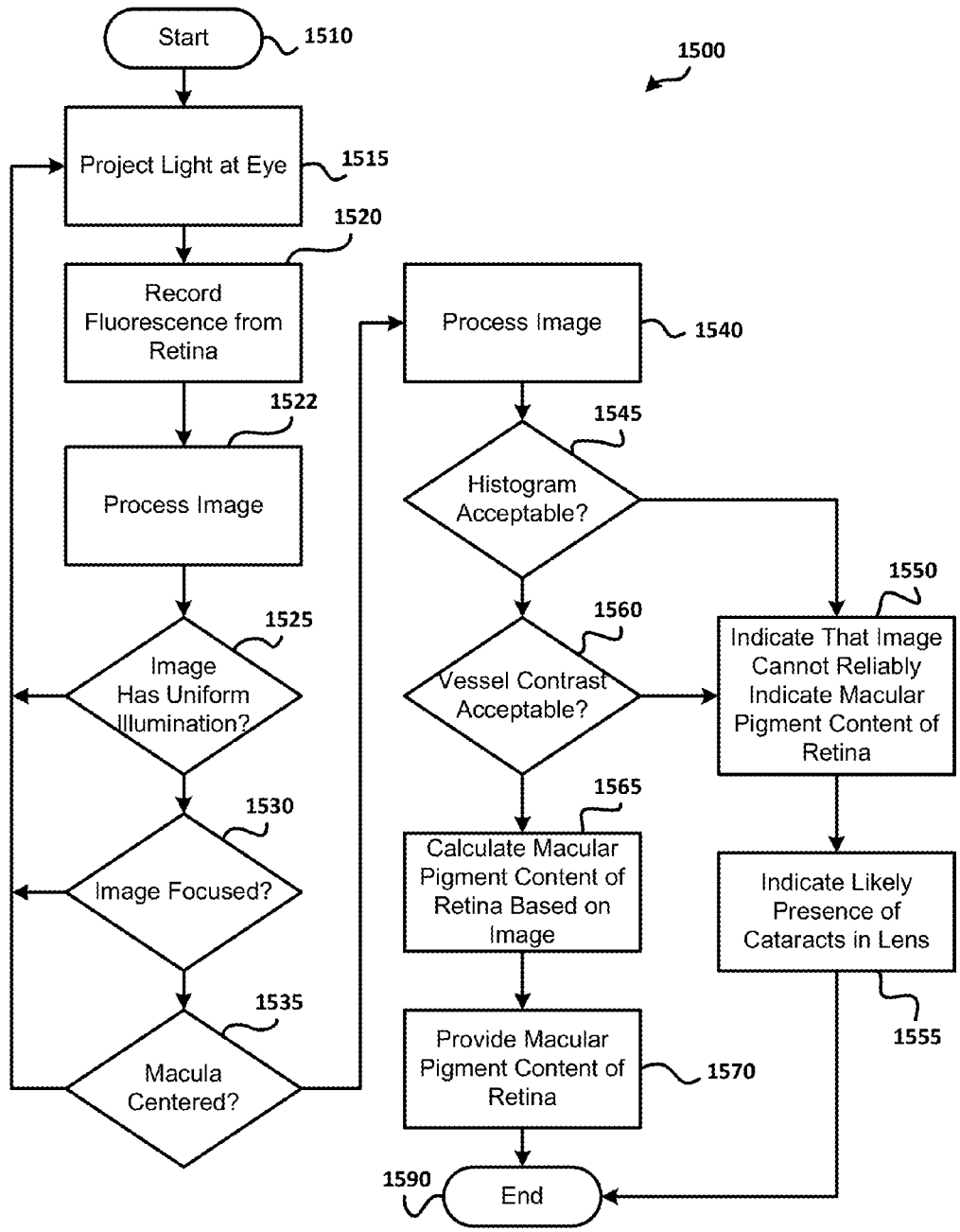
FIG. 15 is a flowchart diagram illustrating one method of obtaining, validating, and/or processing an AFI image, and providing related conclusions and/or output.

Referring to FIG. 15, a flowchart diagram illustrates one method 1500 of obtaining, validating, and/or processing an AFI image, and providing related conclusions and/or output. The method 1500 may start 1510 with a step 1515 in which light is projected at the eye. This may be done, for example, with the optical illumination component 10 of FIG. 1. As used in this application, "light" refers to electromagnetic energy of any wavelength, amplitude, or coherency, and thus is not limited to visible light.

Once retina of the subject eye is properly illuminated, the method 1500 may proceed to a step 1520 in which the AFI image is recorded from light received from the retina. The image may be recorded, for example, with the two-dimensional imaging detector array/video camera 26 of FIG. 1.

Once the AFI image has been recorded, the method 1500 may proceed to a step 1522 in which the AFI image is processed in preparation for the application of the image acceptance criteria. According to some embodiments of the invention, the step 1522 may generate analytical tools that facilitate further analytical steps. These analytical tools may include histograms, two-dimensional line plots, three dimensional line plots, and/or any other tool that can facilitate further analysis. An "analytical tool" may thus be any type of data structure or data visualization that can be used to facilitate analysis. Examples of such tools are illustrated in the preceding Figures.

Once the AFI image has been processed, a number of image acceptance criteria may be applied, as illustrated in a query 1525, a query 1530, and a query 1535. The image acceptance criteria may be applied in a variety of ways, including manual and automatic methods. More specifically, a trained user may view the AFI images and make decisions as to whether the AFI images meet the acceptance criteria. Additionally or alternatively, a computing device such as the computing device 60 of FIG. 1 may be used to automatically apply the image acceptance criteria. Thus, the query 1525, the query 1530, and/or the query 1535 may be carried out by individuals and/or computing devices.

In the query 1525, the AFI image may be checked for uniform illumination. This may be done, for example, as set forth in the description of FIGS. 6 through 7D. If the query 1525 indicates that the subject eye was not properly illuminated, the AFI image may need to be re-taken. Thus, the method 1500 may return to the step 1515 so that the eye can, again, be illuminated and a new AFI image can be captured in the step 1520. The new AFI image may then be processed in the step 1522 in preparation for re-application of the image acceptance criteria.

If the AFI image indicates that the subject eye was properly illuminated, the method 1500 may proceed to the query 1530. In the query 1535, the AFI image may be checked for proper focus. This may be done, for example, as set forth in the description of FIGS. 6 through 7D. If the AFI image is not properly focused, the AFI image may need to be re-taken. Thus, the method 1500 may return to the step 1515 so that the eye can, again, be illuminated and a new AFI image can be captured in the step 1520. The new AFI image may then be processed in the step 1522 in preparation for re-application of the image acceptance criteria.

If the AFI image is properly focused, the method 1500 may proceed to the query 1535. In the query 1535, the AFI image may be checked for proper centering of the macula in the AFI image. This may be done, for example, as set forth in the description of FIG. 4. If the macula is not properly centered, the AFI image may need to be re-taken. Thus, the method 1500 may return to the step 1515 so that the eye can, again, be illuminated and a new AFI image can be captured in the step 1520. The new AFI image may then be processed in the step 1522 in preparation for re-application of the image acceptance criteria.

If the macula is properly centered in the AFI image, the image acceptance criteria may be deemed to be satisfied. Notably, the query 1525, the query 1530, and the query 1535 represent only one of many possible image acceptance criteria schema that may be used according to the present invention. Any of the image acceptance criteria applied in the query 1525, the query 1530, and the query 1535 may be omitted and/or replaced with other image acceptance criteria. Additionally or alternatively, other image acceptance criteria may be added to those of the query 1525, the query 1530, and the query 1535. Image acceptance criteria may be assessed in any order; the order of the query 1525, the query 1530, and the query 1535 in FIG. 15 is merely exemplary.

Once the image acceptance criteria are satisfied, the AFI image may be accepted for further processing without the need for further image recordation. Thus, the method 1500 may proceed to a step 1540 in which the image is processed to provide the data needed for application of the image clarity criteria Like the query 1525, the query 1530, and the query 1535, the step 1540 may be automated or manual, and may thus be carried out by humans, computing devices, and/or combinations thereof.

According to some embodiments of the invention, the step 1540 may generate analytical tools that facilitate further analytical steps. These analytical tools may include histograms, two-dimensional line plots, three dimensional line plots, and/or any other tool that can facilitate further analysis. Examples of such tools are illustrated in the preceding Figures.

Once the AFI image has been processed in the step 1540, a number of image clarity criteria may be applied, as illustrated in a query 1545 and a query 1560. Like the image acceptance criteria, the image clarity criteria may be applied in a variety of ways, including manual and automatic methods. A user and/or a computing device may be used to apply the image clarity criteria, manually and/or in an automated fashion. Thus, the query 1545 and/or the query 1560 may be carried out by individuals and/or computing devices.

In the query 1545, a histogram for the AFI image may be checked to determine whether excessive scattering has occurred. This may be done, for example, by measuring characteristics of the histogram such as the average intensity, base width, and/or the highest pixel count of pixels having the same and/or similar intensity values. Some exemplary techniques for assessing the clarity of an AFI image based on associated pixel intensity histograms are shown and described in connection with FIGS. 8A through 9F. The histogram analysis techniques used to carry out the query 1545 may include, but are not limited to, those set forth previously.

If the histogram is not acceptable, the AFI image may not be sufficiently clear to generate an MPOD measurement with sufficient confidence. Thus, the method 1500 may proceed to a step 1550 in which an indication is provided to a user that the image cannot reliably indicate macular pigment content of the retina. The step 1550 may be carried out manually by a user. However, in the event that the query 1545 is performed by a computing device such as the computing device 60 of FIG. 1, performance of the step 1550 may include displaying a message on a display screen, generating an audible tone, or the like, to provide the indication to a user of the computing device.

This failure of the histogram to satisfy the query 1545 may be due to the presence of one or more cataracts in the lens of the eye. Thus, the method 1500 may also carry out a step 1555 in which an indication is provided to a user that one or more cataracts are likely present in the lens. Hence, even though the primary purpose of the method 1500 may be to detect macular pigment levels in the hope of assessing the presence and/or likelihood of macular degeneration, the method 1500 may also provide a tentative diagnosis of cataracts in the subject eye. Like the step 1550, the step 1555 may be performed manually by a user and/or via an output device such as a display screen connected to a computing device. The method 1500 may then end 1590.

If performance of the query 1545 results in a conclusion that the histogram is acceptable, the method 1500 may proceed instead to the query 1560. In the query 1560, a determination may be made as to whether the level of contrast in the blood vessels is acceptable. This may be done, for example, by measuring characteristics of a blood vessel histogram as shown in FIGS. 12A and 12B. The average intensity, base width, and/or the highest pixel count of pixels having the same and/or similar intensity values may be used to assess blood vessel contrast in the blood vessel histogram. Additionally or alternatively, blood vessel contrast may be measured through the use of a line plot, as shown in FIG. 3. Some exemplary techniques for assessing the blood vessel contrast of an AFI image are shown and described in connection with FIG. 3, FIG. 12A, and FIG. 12B. The analysis techniques used to carry out the query 1560 may include, but are not limited to, those set forth previously.

If the blood vessel contrast level is not acceptable, the AFI image may not be sufficiently clear to generate an MPOD measurement with sufficient confidence. Thus, the method 1500 may proceed to the step 1550 and/or the step 1555 as outlined above.

If the query 1560 determines that the AFI image has sufficient blood vessel contrast, the image clarity criteria may be deemed satisfied. Notably, the query 1545 and the query 1560, represent only one of many possible image clarity criteria schema that may be used according to the present invention. Any of the image clarity criteria applied in the query 1545 and the query 1560 may be omitted and/or replaced with other image clarity criteria. Additionally or alternatively, other image clarity criteria may be added to those of the query 1545 and the query 1560. Image clarity criteria may be assessed in any order; the order of the query 1545 and the query 1560 in FIG. 15 is merely exemplary.

Once the image clarity criteria are satisfied, the macular pigment content of the macula may be calculated and provided to the user. Thus, the method 1500 may proceed to a step 1565 in which the MPOD of the eye is calculated based on the AFI image. Then, in a step 1570, the MPOD may be provided for the user. As in previous steps, the step 1565 and the step 1570 may be automated or manual, and may thus be carried out by humans, computing devices, and/or combinations thereof.

The step 1565 may involve the use of any of the analytical tools generated in previous steps such as the step 1540. Thus, the step 1565 may involve the use of histograms, two-dimensional pixel intensity line plots, three-dimensional spatial pixel intensity distributions, circular line plots, or any other data structure or visualization derived from the AFI image. According to one example, the MPOD level of the eye may be calculated through the use of the procedures shown and described in connection with FIGS. 2A through 2C above. If the AFI image is sufficiently clear, as determined by the image clarity criteria, there may be no need to adjust the resulting MPOD levels, the MPOD levels may be provided to the user in the step 1570 without adjustment.

However, in the event that the AFI image is clear enough to provide the MPOD level with sufficient confidence, but not clear enough to do so without adjustment, the step 1565 may include the application of one or more correction factors to the MPOD level measured from the AFI image. The clinical results presented previously show that the blue illumination wavelength used in AFI imaging is strongly influenced by scattering of anterior ocular media. This may make it possible to use pixel intensity histogram features of the AFI image as well as measured blood vessel contrast values as quantitative indicators for the presence and degree of associated opacities. Thus, the pixel intensity histogram features and/or blood vessel contrast values may be used as image clarity criteria. Since the media opacities are most likely caused by cataracts in elderly subjects, it is possible, therefore, to use the AFI imaging method as a detector for the presence of cataracts. Possible quantitative criteria include, but are not limited to, blood vessel contrast values or pixel intensity histogram widths lying below predetermined threshold values.

According to one embodiment, correction factors that account for anterior ocular occlusions may be obtained based on data generated in the process of assessing the image clarity criteria. Any of the image clarity criteria may provide a numerical measurement of the clarity of the AFI image. Such a measurement may be used to not only resolve the query by determining whether the AFI image is sufficiently clear to indicate the macular pigment level of the eye with confidence, but also indicate how much correction of the MPOD level measured in the image is needed to account for the light scattering caused by cataracts or other anterior ocular occlusions.

According to one embodiment, the base width of the AFI image pixel intensity histogram, as shown in the exemplary histograms of FIGS. 8C, 8D, 9C, and 9D, may be measured. This base width may be used in combination with the plot of FIG. 14 (or with an equation representing the plot of FIG. 14) to obtain the appropriate correction factor for the MPOD level based on the base width of the AFI image pixel intensity histogram.

Once the appropriate correction factor has been determined, the MPOD level (for example, measured as set forth in FIGS. 2A through 2C above, may be multiplied by the correction factor to obtain the corrected MPOD level. This corrected MPOD level may then be provided to the user in the step 1570. The method 1500 may then end 1590.

Notably, the method 1500 is only one example of many methods that may be used according to the present invention. In other embodiments, only a single processing step, such as the step 1522 or the step 1540, may be used in preparation for application of the image acceptance criteria and the image clarity criteria. The image acceptance criteria and/or the image clarity criteria may be omitted, either in part or as a whole. Other categories of criteria based on other aspects of the AFI image may be applied, in place of or in addition to the image acceptance criteria and/or the image clarity criteria. The various steps and queries of the method 1500 may also be re-ordered in a wide variety of ways. Various user indications and/or reports may be generated and/or provided to the user.

It may be helpful to compare AFI image degradation levels quantified with objective parameters such as blood vessel contrast and histogram pixel intensity width with the severity of cataracts assessed by subjective visual expert inspection. The latter uses a lens opacity classification system, LOCS, and assesses scores for the degree of incident cortical, nuclear, and posterior sub-capsular opacities, indicated by a set of three respective numbers.

Referring to FIGS. 16A through 16I, nine AFI images are shown along with associated lens opacity scores. More specifically, AFI images are shown for three sets of subjects, with three different subjects in each set. Even though the subjects' eyes have been diagnosed with identical LOCS scores in each set, as indicated by the respective scores, the AFI images show drastic differences in image quality between subjects of the same set. For example, in the set with identical LOCS scores of 3-2-2, shown in FIGS. 16D through 16F, the AFI image of one subject's eye is relatively clear, as shown in FIG. 16D, while the AFI image of another subject's eye is barely visible as shown in FIG. 16E, while the subject eye of FIG. 16F has an AFI image with relatively strong scattering, but with key landmark features still recognizable. Based on these results it appears that the AFI imaging method may be suitable as an objective detector for lens opacities that exceeds, in its precision, the subjective scoring of lens opacities, which at present is used most widely in the diagnosis of cataracts.

In healthy subjects, the lipofuscin chromophores are typically relatively evenly distributed over the retinal pigment epithelial layer. Lipofuscin intensity levels may therefore correlate with the illumination intensity distribution over the illuminated retina, having maximum levels in the macular region and dropping off slowly, i.e. monotonously, towards the retinal periphery. There should be no sharp dips in lipofuscin intensities in retinal areas other than in the key landmark features (macula, blood vessels, and optic disk). Deviations of lipofuscin intensity levels from the normal behavior can therefore be used as indicator for the existence of retinal pathologies.

Figure 17A:
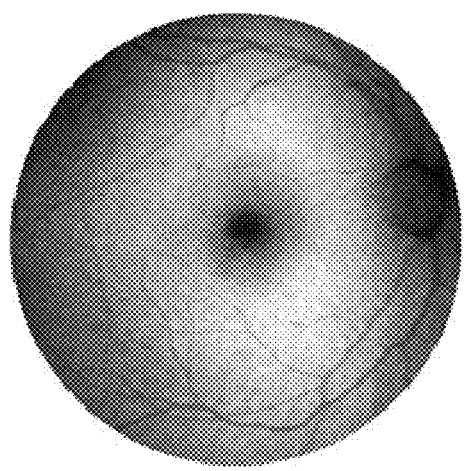
FIGS. 17A and 17B are AFI images of a healthy eye and an eye with pathology in the macular area.
Figure 17B:
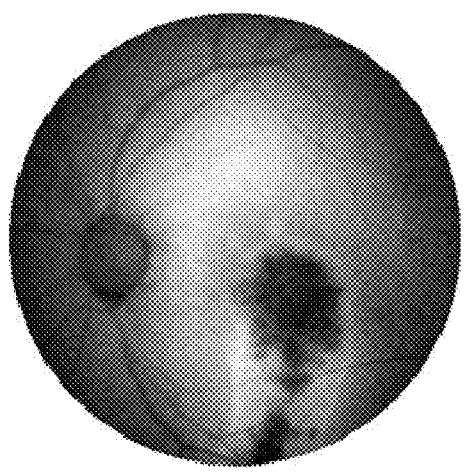
Figure 17C:
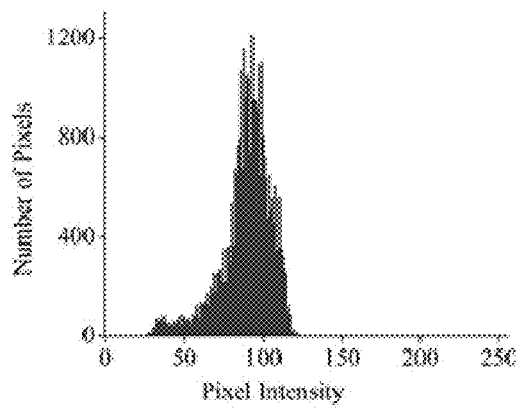
FIGS. 17C and 17D are pixel intensity histograms corresponding to the AFI images of FIGS. 17A and 17B, respectively.
Figure 17D:
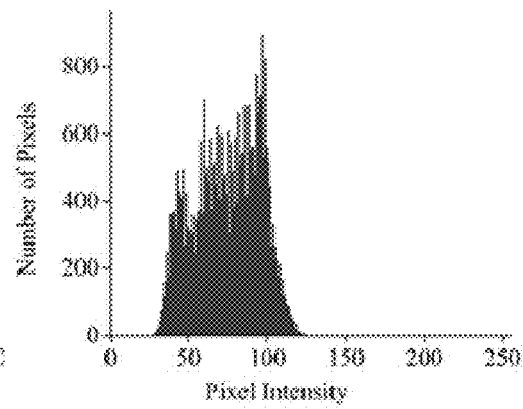

Referring to FIGS. 17A through 17D, AFI images and pixel intensity histograms are shown for a healthy eye and an eye with a pathology. More specifically, FIG. 17A is an AFI image for a healthy eye and FIG. 17B is an AFI image for an eye with a pathology. FIG. 17C is the histogram for the eye of FIG. 17A and FIG. 17D is the pixel intensity histogram for the eye of FIG. 17B.

FIGS. 17A through 17D illustrate the use of AFI images and related data to diagnose pathologies. In FIG. 17B, the AFI image is shown for a subject eye with an abnormal lipofuscin distribution in the macular region. The pathology is clearly visible in the AFI image, particularly when it is compared with the AFI image for a subject eye with a normal distribution, as shown in FIG. 17A.

FIGS. 17C and 17D show the pixel intensity histograms. The pixel intensity histogram for the AFI image with abnormality, shown in FIG. 17D, reveals a much higher number of pixels at low intensities relative to the histogram of a normal AFI image. It appears possible, therefore, to use abnormal deviations of histogram characteristics, such as an unusually large deviation of the number of pixel intensities at low intensities from normal pixel numbers, as an indicator for the presence of abnormalities. This information could be used to judge the processing of MP characteristics as problematic and to display a corresponding message. Similar abnormalities could be visible in AFI images from subjects with other retinal pathologies such as drusen, scars, and the like.

Thus, pre-established pixel number ranges at low pixel intensities could be used as criteria for the exclusion of eyes with pathologies. This may be done, for example, by applying additional image criteria that assess whether an AFI image is likely to indicate such a pathology ("pathology criteria"). Such pathology criteria may be image acceptance criteria, image clarity criteria, or applied independently of the image acceptance criteria and the image clarity criteria. Thus, pathology criteria may be independent of the image acceptance criteria and/or the image clarity criteria. The method 1500 may be modified to apply one or more pathology criteria and to return an error message in the event of detection of a pathology, to indicate the likely type or severity of the pathology, and/or to generate MPOD data for the subject eye regardless of the existence of the pathology.

Further, with the aid of the systems and methods of the present invention, it may be possible to also see fine structures in the spatial profile of the macular pigment distributions of subject eyes by enlarging the AFI image. Analytical steps may be performed on the enlarged AFI image to more clearly visualize and/or analyze such features.

Figure 18A:
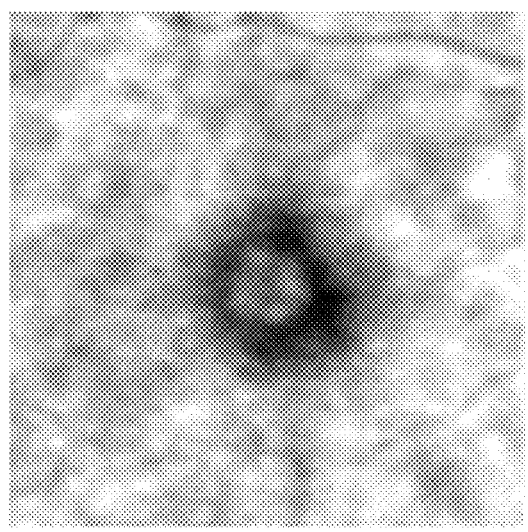
FIG. 18A is an enlarged AFI image for an eye with a macular pigment ring fine structure.
Figure 18B:
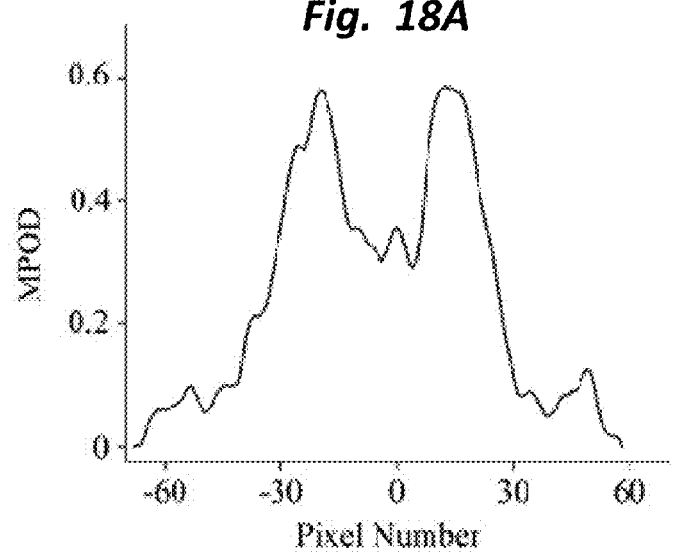
FIGS. 18B and 18C are an enlarged pixel intensity line plot and an enlarged three-dimensional spatial intensity distribution, respectively, for the enlarged AFI image of FIG. 18A.
Figure 18C:
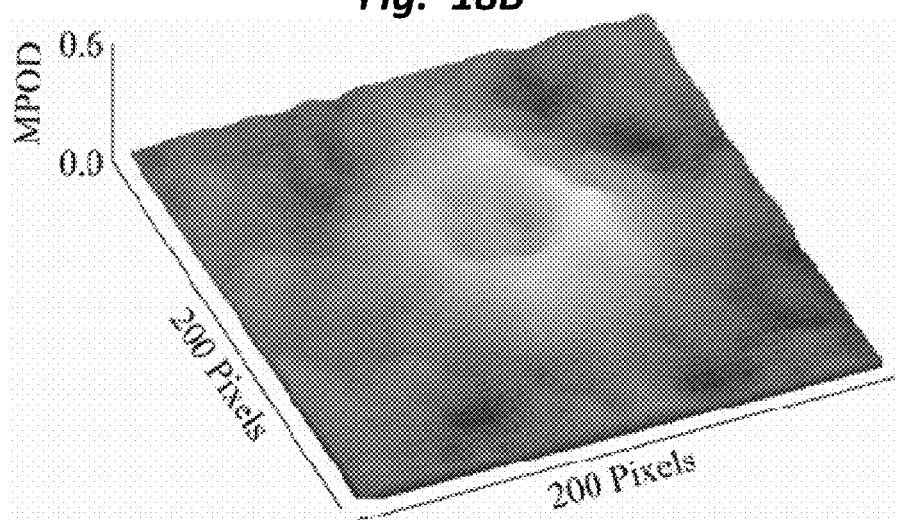

Referring to FIGS. 18A, 18B, and 18C, visualization and analysis of such fine structures are shown. More precisely, FIG. 18A is an enlarged AFI image for an eye with a macular irregularity. The enlarged AFI image may be a macula-centered portion of an AFI image like those shown previously. FIGS. 18B and 18C are an enlarged pixel intensity line plot and an enlarged three-dimensional spatial intensity distribution, respectively, for the enlarged AFI image of FIG. 18A.

As shown, the subject eye appears to have a ring-shaped circular pigment distribution, which may not be generally visible in an AFI image (not shown) from which the enlarged AFI image of FIG. 18A is obtained. The enlarged AFI image of FIG. 18A may more clearly show the macular pigment fine structure, which may result in a ring-shaped distribution of macular pigment levels with a central dip, as evidenced by the enlarged AFI image of FIG. 18A, the MPOD line plot running through the macula shown in FIG. 18B, and the three-dimensional spatial intensity distribution of FIG. 18C.

The macular pigment fine structure may be indicative of various conditions of the eye. Enlarged views like that of FIG. 18A and/or enlarged analytical tools like those of FIGS. 18B and 18C may be used to assess the condition of the subject eye in greater detail, including a more detailed analysis of macular pigment levels, diagnosis of other eye conditions besides macular degeneration, or the like.

Figure 19:
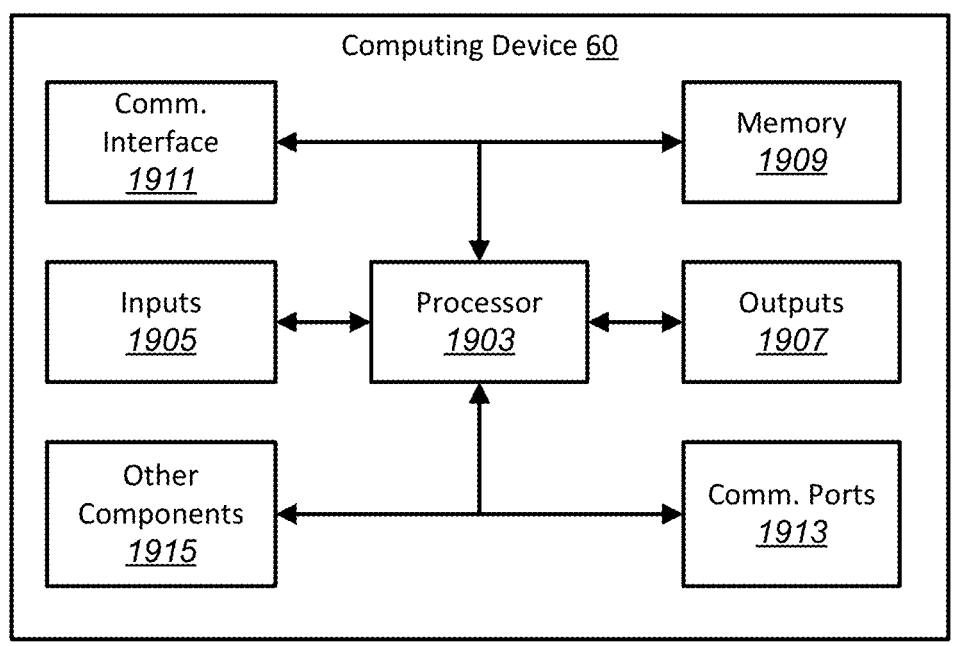
FIG. 19 is a schematic block diagram illustrating a computing device that may be used in certain embodiments of the invention.

Referring to FIG. 19, a schematic block diagram illustrates various hardware components that may be used in a computing device such as the computing device 60 of the optical system 100 of FIG. 1. The computing device 60 may include a processor 1903 in electronic communication with input components or input devices 1905 and/or output components or output devices 1907. The processor 1903 may be operably connected to input devices 1905 and/or output devices 1907 capable of electronic communication with the processor 1903, or, in other words, to devices capable of input and/or output in the form of an electrical signal. The computing device 60 may include the input devices 1905, output devices 1907, and/or the processor 1903 within the same physical structure or in separate housings or structures.

The computing device 60 may also include memory 1909. The memory 1909 may be a separate component from the processor 1903, or it may be on-board memory 1909 included in the same part as the processor 1903. For example, microcontrollers often include a certain amount of on-board memory. The memory 1909 may store information such as lipofuscin levels, AFI images, two-dimensional line plots, three-dimensional spatial intensity distributions, circular line plots, histograms, and/or other information that may be used with the present systems and methods.

The processor 1903 may also be in electronic communication with a communication interface 1911. The communication interface 1911 may be used for communications with other devices such as other computing devices 60 and/or other components of the optical system 100. For example, the communication interface 1911 may be used to communicate with the optical illumination component 10 and/or the image recording component 20 of FIG. 1. If desired, the computing device 60 may act as a controller for the optical system 100, and may thus control the operation of the other components. Additionally or alternatively, multiple computing devices 60 may be used, and the communication interfaces 1911 of the computing devices 60 may be designed to communicate with each other to send signals or messages between computing devices 60.

The computing device 60 may also include other communication ports 1913. In addition, other components 1915 may also be included in the computing device 60.

The computing device 60 may have a wide variety of architectures, software components, and or hardware components. In some examples, the computing device 60 may be a one-chip computer, such as a microcontroller, a one-board type of computer, such as a controller, a desktop computer running Linux, Unix, Windows, MacOS, or any other operating system, a tablet, a smartphone, a Personal Digital Assistant (PDA), a Unix-based workstation, a smart phone, or the like. Accordingly, the block diagram of FIG. 19 is only meant to illustrate typical components of a computing device 60 and is not meant to limit the scope of examples disclosed herein.

The various illustrative logical blocks, modules, circuits and algorithm steps described in connection with the examples disclosed herein may be implemented as electronic hardware, computer software or combinations of both. To illustrate this interchangeability of hardware and software, various illustrative components, blocks, modules, circuits and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Where the described functionality is implemented as computer software, such software may include any type of computer instruction or computer executable code located within a memory device and/or transmitted as electronic signals over a system bus or network. Software that implements the functionality associated with components described herein may comprise a single instruction, or many instructions, and may be distributed over several different code segments, among different programs, and across several memory devices.

The various illustrative logical blocks, modules, and circuits described in connection with the examples disclosed herein may be implemented or performed with a general purpose processor, a digital signal processor (DSP), an application specific integrated circuit (ASIC), a field programmable gate array signal (FPGA) or other programmable logic device, discrete gate or transistor logic, discrete hardware components or any combination thereof designed to perform the functions described herein. A general-purpose processor may be a microprocessor, but in the alternative, the processor may be any conventional processor, controller, microcontroller or state machine. A processor may also be implemented as a combination of computing devices, e.g., a combination of a DSP and a microprocessor, a plurality of microprocessors, one or more microprocessors in conjunction with a DSP core or any other such configuration.

The steps of a method or algorithm described in connection with the examples disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM or any other form of storage medium known in the art. An exemplary storage medium may be coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The word "exemplary" is used exclusively herein to mean "serving as an example, instance, or illustration." Any example described herein as "exemplary" is not necessarily to be construed as preferred or advantageous over other examples.

The term "determining" (and grammatical variants thereof) is used in an extremely broad sense. The term "determining" encompasses a wide variety of actions and therefore "determining" can include calculating, computing, processing, deriving, investigating, looking up (e.g., looking up in a table, a database or another data structure), ascertaining and the like. In addition, "determining" can include receiving (e.g., receiving information), accessing (e.g., accessing data in a memory) and the like. In addition, "determining" can include resolving, selecting, choosing, establishing and the like.

The phrase "based on" does not mean, "based only on," unless expressly specified otherwise. In other words, the phrase "based on" describes both "based only on" and "based at least on."

The methods disclosed herein comprise one or more steps or actions for achieving the described method. The method steps and/or actions may be interchanged with one another without departing from the scope of the present invention. In other words, unless a specific order of steps or actions is required for proper operation of the example, the order and/or use of specific steps and/or actions may be modified without departing from the scope of the present system and methods described herein.

While specific examples and applications of the present system and methods described herein have been illustrated and described, it is to be understood that the invention is not limited to the precise configuration and components disclosed herein. Various modifications, changes and variations, which will be apparent to those, skilled in the art may be made in the arrangement, operation, and details of the methods and systems of the present invention disclosed herein without departing from the spirit and scope of the invention.

What is claimed is:

1. A method for diagnosing a condition of an eye, the method comprising:
   projecting light at the eye;
   recording lipofuscin fluorescence from a retina of the eye to form a first image of the retina;
   processing the first image to make an image clarity determination regarding a level of conformance of the first image to at least one image clarity criterion, comprising:
      creating a pixel intensity histogram for the first image of recorded lipofuscin fluorescence; and
      assessing a base width of the pixel intensity histogram;
   determining whether the first image can reliably indicate a macular pigment content of the retina based on the image clarity determination; and
   calculating the macular pigment content of the retina, comprising:
      measuring the macular pigment content based on the image;
      determining a correction factor that is derived from the base width of the pixel intensity histogram, wherein the correction factor adjusts the macular pigment content to account for at least one cataract in the eye, wherein the correction factor decreases with increasing base widths; and
      multiplying the measured macular pigment content by the correction factor to determine an estimated macular pigment content of the retina that would be measured if the at least one cataract was removed from the eye.

2. The method of claim 1, wherein projecting light at the eye and recording lipofuscin fluorescence from the retina define a lipofuscin fluorescence excitation spectroscopy process, wherein the first image comprises a two-dimensional lipofuscin intensity pixel map.

3. The method of claim 1, wherein processing the first image to make the image clarity determination further comprises:
   receiving the image in a computing device;
   generating at least one analytical tool based on the image;
   analyzing the analytical tool; and
   based on results of analysis of the analytical tool, making the image clarity determination.

4. The method of claim 1, further comprising:
   processing the first image to make an image acceptance determination that the first image does not conform to at least one image acceptance criterion; and
   based on the image acceptance determination, recording lipofuscin fluorescence from a retina of the eye to form a second image of the retina.

5. The method of claim 4, wherein the image acceptance criterion is selected from the group consisting of:
   whether the macula is centered in the first image;
   whether the first image is properly focused; and
   whether the eye was properly illuminated when the first image was taken.

6. The method of claim 1, wherein processing the first image to make the image clarity determination further comprises:
   based on the base width, calculating a level of clarity of the first image.

7. The method of claim 1, wherein processing the first image to make the image clarity determination further comprises:
   creating a line plot of pixel intensities for the first image;
   based on the line plot, assessing a level of contrast between retinal blood vessels and surrounding retinal tissue; and
   based on the level of contrast, calculating a level of clarity of the first image.

8. The method of claim 1, further comprising concluding that a cataract is present in a lens of the eye based on the image clarity determination.

9. A computer program product for diagnosing a condition of an eye, the computer program product comprising:
   a non-transitory storage medium; and
   computer program code encoded on the non-transitory storage medium, wherein the computer program code is configured to cause at least one processor to perform the steps of:
      receiving a first image of a retina of the eye, wherein the first image comprises a lipofuscin fluorescence intensity pixel map;
      processing the first image to make an image clarity determination regarding a level of conformance of the first image to at least one image clarity criterion, comprising:
         creating a pixel intensity histogram for the first image of recorded lipofuscin fluorescence; and
         assessing a base width of the pixel intensity histogram;
      determining whether the first image can reliably indicate a macular pigment content of the retina based on the image clarity determination; and
      calculating the macular pigment content of the retina only if the first image can be used to reliably indicate the macular pigment content of the retina, comprising:
         measuring the macular pigment content based on the image;
         determining a correction factor that is derived from the base width of the pixel intensity histogram, wherein the correction factor adjusts the macular pigment content to account for at least one cataract in the eye, wherein the correction factor decreases with increasing base widths; and
         multiplying the measured macular pigment content by the correction factor to determine an estimated macular pigment content of the retina that would be measured if the at least one cataract was removed from the eye.

10. The computer program product of claim 9, wherein the computer program code is further configured to cause the at least one processor to perform the steps of:
    processing the first image to make an image acceptance determination that the first image does not conform to at least one image acceptance criterion; and
    based on the image acceptance determination, initiating recordation of lipofuscin fluorescence from a retina of the eye to form a second image of the retina.

11. The computer program product of claim 9, wherein the computer program code is further configured to cause the at least one processor to process the first image to make the image clarity determination by:
    based on the base width, calculating a level of clarity of the first image.

12. The computer program product of claim 9, wherein the computer program code is further configured to cause the at least one processor to process the first image to make the image clarity determination by:

creating a line plot of pixel intensities for the first image;
based on the line plot, assessing a level of contrast between retinal blood vessels and surrounding retinal tissue; and
based on the level of contrast, calculating a level of clarity of the first image.

13. A system for diagnosing a condition of an eye, the system comprising:
a processor configured to:
receive a first image of a retina of the eye, wherein the first image comprises a lipofuscin fluorescence intensity pixel map;
process the first image to make an image clarity determination regarding a level of conformance of the first image to at least one image clarity criterion, comprising:
creating a pixel intensity histogram for the first image of recorded lipofuscin fluorescence; and
assessing a base width of the pixel intensity histogram;
determine whether the first image can reliably indicate a macular pigment content of the retina based on the image clarity determination; and
calculate the macular pigment content of the retina only if the first image can be used to reliably indicate the macular pigment content of the retina, comprising:
measuring the macular pigment content based on the image;
determining a correction factor that is derived from the base width of the pixel intensity histogram, wherein the correction factor adjusts the macular pigment content to account for at least one cataract in the eye, wherein the correction factor decreases with increasing base widths; and
multiplying the measured macular pigment content by the correction factor to determine an estimated macular pigment content of the retina that would be measured if the at least one cataract was removed from the eye.

14. The system of claim 13, wherein the processor is further configured to:
process the first image to make an image acceptance determination that the first image does not conform to at least one image acceptance criterion; and
based on the image acceptance determination, initiate recordation of lipofuscin fluorescence from a retina of the eye to form a second image of the retina.

15. The system of claim 13, wherein the processor is further configured to process the first image to make the image clarity determination by:
based on the base width, calculating a level of clarity of the first image.

16. The system of claim 13, wherein the processor is further configured to process the first image to make the image clarity determination by:
creating a line plot of pixel intensities for the first image;
based on the line plot, assessing a level of contrast between retinal blood vessels and surrounding retinal tissue; and
based on the level of contrast, calculating a level of clarity of the first image.

17. The system of claim 13, further comprising an optical system configured to:
project light at the eye; and
record lipofuscin fluorescence from a retina of the eye to form the first image.

* * * * *